US010289280B2

(12) United States Patent
Joglekar et al.

(10) Patent No.: US 10,289,280 B2
(45) Date of Patent: May 14, 2019

(54) DETERMINING VERTICAL AXIS SCALE FOR IMPLANTABLE FLUID DELIVERY SYSTEM

(71) Applicant: Medtronic, Inc., Minneapolis, MN (US)

(72) Inventors: Ajinkya M. Joglekar, Maple Grove, MN (US); Bradley C. Peck, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 852 days.

(21) Appl. No.: 13/913,324

(22) Filed: Jun. 7, 2013

(65) Prior Publication Data

US 2014/0365941 A1 Dec. 11, 2014

(51) Int. Cl.
*G06F 3/0484* (2013.01)
*G06F 19/00* (2018.01)
*G06T 11/20* (2006.01)
*A61M 5/142* (2006.01)
*G16H 40/63* (2018.01)

(52) U.S. Cl.
CPC ....... *G06F 3/0484* (2013.01); *A61M 5/14276* (2013.01); *G06F 19/00* (2013.01); *G06F 19/3468* (2013.01); *G06T 11/206* (2013.01); *A61M 2205/502* (2013.01); *G16H 40/63* (2018.01)

(58) Field of Classification Search
CPC ............... G06F 3/0484; G06F 19/3468; G06F 19/3406; G06T 11/206; A61M 2005/14208
See application file for complete search history.

(56) References Cited

U.S. PATENT DOCUMENTS 6,245,349 B1 * 6/2001 Yiv .................. A61K 9/1075
424/400
6,812,926 B1 11/2004 Rugge
2007/0083152 A1 4/2007 Williams, Jr. et al.
(Continued)

FOREIGN PATENT DOCUMENTS

EP 1465114 A2 10/2004

OTHER PUBLICATIONS

International Search Report and Written Opinion from International Application No. PCT/US2014/034154, dated Nov. 6, 2014, 12 pp.

*Primary Examiner* — Seth A Silverman
(74) *Attorney, Agent, or Firm* — Shumaker & Sieffert, P.A.

(57) ABSTRACT

A device for programming an implantable fluid delivery device receives a therapeutic agent concentration, wherein the therapeutic agent concentration comprises a mass of the therapeutic agent per unit of volume. The device further determines a reference rate value based on the received therapeutic agent concentration, wherein the reference rate value comprises a mass per unit of time. The device additionally displays a graphical user interface comprising a horizontal axis and a vertical axis, wherein the horizontal axis represents time and the vertical axis represents rates of delivery of the fluid by the implantable fluid delivery device. The maximum value of the vertical axis displayed in the graphical user interface is determined based on the determined reference rate value and is determined to be less than a maximum therapeutic agent infusion rate.

40 Claims, 20 Drawing Sheets

(56) References Cited

U.S. PATENT DOCUMENTS

| | | | |
|---|---|---|---|
| 2007/0093786 A1* | 4/2007 | Goldsmith et al. | 604/890.1 |
| 2008/0119705 A1 | 5/2008 | Patel et al. | |
| 2010/0010646 A1* | 1/2010 | Drew | A61M 5/14276 |
| | | | 700/86 |
| 2010/0185183 A1* | 7/2010 | Alme | A61M 5/14276 |
| | | | 604/891.1 |
| 2010/0188427 A1* | 7/2010 | Chuang | G06Q 10/00 |
| | | | 345/660 |

* cited by examiner

DETERMINING VERTICAL AXIS SCALE FOR IMPLANTABLE FLUID DELIVERY SYSTEM

TECHNICAL FIELD

This disclosure relates to implantable medical devices, and, more particularly, to programming of implantable medical devices.

BACKGROUND

A variety of medical devices are used for chronic, i.e., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician. The devices may be implantable medical devices that receive the program from a programmer controlled by the clinician.

Examples of such implantable medical devices include implantable fluid delivery devices, implantable neurostimulators, implantable cardioverters, implantable cardiac pacemakers, implantable defibrillators, cochlear implants, and other devices that now exist or may exist in the future. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device configured to deliver a fluid medication to a patient at a selected site. A drug infusion device may be implanted at a location in the body of a patient and deliver a fluid medication through an implanted catheter to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the implantable medical device (IMD) of a fluid delivered to the patient.

Programmable implantable medical devices are typically programmed using an external instrument, sometimes referred to as a controller or programmer, as mentioned above, that communicates with the implanted medical device via wireless telemetry. A user, such as a patient or a medical professional, can control the programmer to adjust parameters associated with therapy delivered by the implanted medical device. For example, the user may control the programmer to increase or decrease an amount or rate of delivery of fluid medication delivered to the patient. Typically, a user interacts with the programmer to set various parameters, which are then transmitted to the implanted medical device.

SUMMARY

In general, this disclosure describes techniques for automatically setting a vertical axis scale for an implantable fluid delivery system. A programmer of an implantable fluid delivery system may display an infusion graph representing an amount, or dose, of a therapeutic agent delivered by the system. The vertical axis scale of the infusion graph represents a rate of therapeutic agent infusion, e.g., in terms of the amount of therapeutic agent pumped or otherwise delivered by the implantable fluid delivery system per unit of time. The programmer may automatically set the vertical axis scale, for example, by adjusting the minimum and/or maximum values of a displayed vertical axis, based on the concentration of the therapeutic agent delivered by the fluid delivery system.

In one example, a method comprises receiving, by a device for programming an implantable fluid delivery device, a therapeutic agent concentration, wherein the therapeutic agent concentration indicates a mass of a therapeutic agent per unit of volume of a fluid delivered by the implantable fluid delivery device. The method further comprises determining, by the device for programming the implantable fluid delivery device, a reference rate value based on the received therapeutic agent concentration, wherein the reference rate value comprises a mass per unit of time. The method also comprises displaying, with the device for programming the implantable fluid delivery device, a graphical user interface comprising a horizontal axis and a vertical axis, wherein the horizontal axis represents time and the vertical axis represents rates of delivery of the fluid by the implantable fluid delivery device, wherein a maximum value of the vertical axis displayed in the graphical user interface is determined based on the determined reference rate value, and wherein the maximum value of the displayed vertical axis is determined to be less than a maximum infusion rate.

In another example, a programmer device comprises a user interface comprising a display to present a graphical representation of delivery of a therapeutic agent to a patient via a fluid by an implantable fluid delivery device, wherein the user interface displays a horizontal axis and a vertical axis, wherein the horizontal axis represents time and the vertical axis represents rates of delivery of the fluid by the implantable fluid delivery device. The programmer device further comprises a processor configured to receive a therapeutic agent concentration, wherein the therapeutic agent concentration indicates a mass of a therapeutic agent per unit of volume of a fluid delivered by the implantable fluid delivery device, determine a reference rate value based on the received therapeutic agent concentration, wherein the reference rate value comprises a mass per unit of time, and control the user interface to display the vertical axis including a maximum value of the vertical axis, wherein the maximum value of the vertical axis displayed in the graphical user interface is determined based on the determined reference rate value, and wherein the maximum value of the displayed vertical axis is determined to be less than a maximum infusion rate.

In another example, a system comprises an implantable fluid delivery device that delivers fluid to a patient according to a dosing program, comprising a computer-readable medium to store the dosing program and a telemetry module. The system further comprises a programmer device, and the programmer device comprises a user interface comprising a display to present a graphical representation of delivery of a therapeutic agent to a patient via a fluid by an implantable fluid delivery device, wherein the user interface displays a horizontal axis and a vertical axis, wherein the horizontal axis represents time and the vertical axis represents rates of delivery of the fluid by the implantable fluid delivery device.

The programmer device further comprises a processor configured to receive a therapeutic agent concentration, wherein the therapeutic agent concentration indicates a mass of a therapeutic agent per unit of volume of a fluid delivered by the implantable fluid delivery device, determine a reference rate value based on the received therapeutic agent concentration, wherein the reference rate value comprises a mass per unit of time, and control the user interface to display the vertical axis including a maximum value of the vertical axis, wherein the maximum value of the vertical axis displayed in the graphical user interface is determined based on the determined reference rate value, and wherein the maximum value of the displayed vertical axis is determined to be less than a maximum infusion rate.

In another example, a medical device comprises means for receiving a therapeutic agent concentration, wherein the therapeutic agent concentration indicates a mass of the therapeutic agent per unit of volume of a fluid delivered by the implantable fluid delivery device. The medical device further comprises means for determining a reference rate value based on the received therapeutic agent concentration, wherein the reference rate value comprises a mass per unit of time and means for displaying a graphical interface comprising a horizontal and a vertical axis, wherein the horizontal axis represents time and the vertical axis represents rates of delivery of the fluid by the implantable fluid delivery device, wherein a maximum value of the vertical axis displayed in the graphical user interface is determined based on the determined reference rate value, and wherein the maximum value of the displayed vertical axis is determined to be less than a maximum infusion rate.

In another example, a computer-readable medium, such as a computer-readable storage medium, contains, e.g., is encoded with, instructions that cause a programmable processor to receive therapeutic agent concentration, wherein the therapeutic agent concentration indicates a mass of a therapeutic agent per unit of volume of a fluid delivered by the implantable fluid delivery device. The instructions further cause the programmable processor to determine a reference rate value based on the received therapeutic concentration, wherein the reference rate value comprises a mass per unit of time and to control a user interface to display a horizontal axis and a vertical axis, wherein the horizontal axis represents time and the vertical axis represents rates of delivery of the fluid by the implantable fluid delivery device, wherein a maximum value of the vertical axis displayed in the graphical user interface is determined based on the determined reference rate value, and wherein the maximum value of the displayed vertical axis is determined to be less than a maximum infusion rate.

The details of one or more example are set forth in the accompanying drawings and the description below. Other features, objects, and advantages will be apparent from the description and drawings, and from the claims.

DETAILED DESCRIPTION

Figure 1:
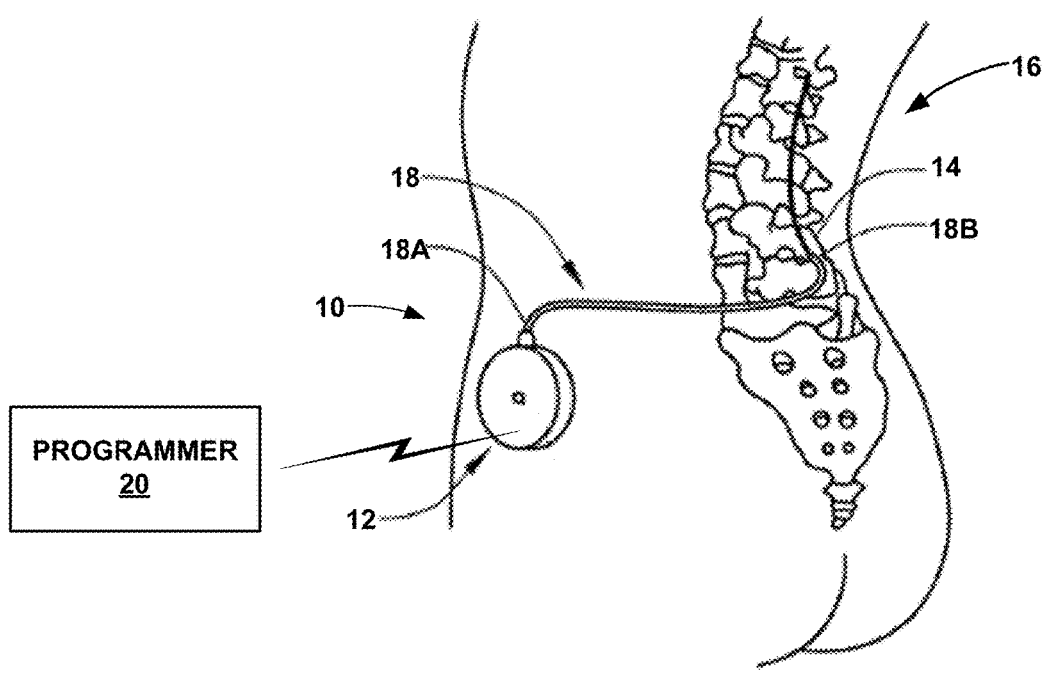
FIG. 1 is a conceptual diagram illustrating an example of an implantable fluid delivery system.

Medical devices are useful for treating, managing or otherwise controlling various patient conditions or disorders, such as, but not limited to, pain (e.g., chronic pain, postoperative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, hypertension, or other disorders. Some medical devices may be configured to deliver one or more therapeutic agents, alone or in combination with other therapies, such as electrical stimulation, to one or more target sites within a patient. For example, in some cases, a medical device may deliver insulin to a patient with diabetes. As another example, a medical device may deliver a pain relief agent to a patient with chronic pain. The medical device may be implanted in the patient for chronic therapy delivery (e.g., longer than a temporary, trial basis).

In general, this disclosure describes techniques for determining vertical axes scales, which also may be referred to as y-axes scales for an infusion graph displayed in a graphical interface of a programmer of an implantable fluid delivery system. The implantable fluid delivery system may deliver different therapeutic agents based on specific patient needs, i.e., the conditions or disorders from which the patient suffers. In some examples, the therapeutic agent may be conventional drugs, such as insulin, pain medication, anti-seizure medications, and the like that are intended to treat one or more patient disorders or conditions. Each different therapeutic agent may be stored in different concentrations by the system. As one illustration, an implantable fluid delivery system may store a first therapeutic agent at a concentration of 10 mg/mL. As another illustration, the implantable fluid delivery system may store a second therapeutic agent at a concentration of 50 mcg/mL. As described below, the differing concentrations of the various therapeutic agents may present design challenges for graphical infusion systems, i.e. systems in which infusion rates can be graphically programmed.

An implantable fluid delivery system may operate according to a graphical infusion programming method. In such a system, a user may program the implantable fluid delivery system to deliver a selected therapeutic agent according to an infusion graph displayed on a display device of the implantable fluid delivery system. For example, implantable fluid delivery systems generally operate according to various dosing parameters, such as dosing time, e.g., the amount of time spent delivering the selected therapeutic agent, and a dosing rate, e.g., the rate at which the fluid delivery system delivers the selected therapeutic agent. In graphical infusion systems, the programming device, or another component of the implantable fluid delivery system, may include a display device that displays a graph including a horizontal axis (or x-axis) and a vertical axis (or y-axis), which correspond to the dosing parameters. Generally, the x-axis may be broken into discrete time segments, e.g., 10 minute segments, 1 hour segments, 1 day segments, or any other time segments. The y-axis of such systems generally corresponds to rate values. For example, each y-axis value may represent a particular rate at which the implantable fluid delivery system delivers the selected therapeutic agent, usually expressed in units of mass per units of time.

In such examples, a user, such as a clinician or a patient, may select or create one or more graphical objects on the graphical interface of the display device. The graphical object may be similar to a bar in a standard bar graph. The bar may span a number of time units and the height of the bar on the y-axis corresponds to a particular therapeutic agent delivery rate. As one illustrative example, a user may create or select a graphical object on the display that spans the hours of 10:00 am to 12:00 pm and has a height corresponding to a therapeutic agent delivery rate of 1 mg per hour. According to this programming, the device may then deliver a selected therapeutic agent at a rate of 1 mg/hour beginning at 10:00 am and ending at 12:00 pm.

These types of graphical infusion interfaces for graphical infusion systems provide a number of ease-of-use advantages over other, more traditional, programming interfaces, such as inputting the various dosing parameters as numbers via text input. For example, a user may more easily adjust the dosing parameters by selecting the bar and increasing/decreasing the height or expanding/contracting the base, e.g., by expanding, contracting, or the like. This style of programming does not require inputting numbers via text input.

However, such a graphical infusion system may present design challenges. For example, in order for a user to select a graphical object to adjust the dosing parameters, the graphical object ordinarily should meet certain size requirements for the display device to detect an external input, e.g., a finger, a stylus, or the like, used in selecting the various features of the graphical object. If the graphical object is too small, a user may have difficulty selecting one or both sides of the graphical object in order to expand/contract the base in order to shorten or lengthen the dosing time. If the graphical object is too small, a user may further have difficulty selecting the top portion of the graphical object in order to increase or decrease the height of the graphical object, thereby adjusting the therapeutic agent infusion rate. In other examples, the graphical object may extend beyond the display range of the display device. In these situations, the user may not be able to select the top portion of the graphical object in order to adjust height up or down to adjust the dosing rate. Since some different therapeutic agents may be stored at different concentrations, there may be no single universal default scale for the y-axis, i.e. the maximum rate value displayed on the y-axis, that will work for every therapeutic agent concentration without creating these types of scale issues. For example, a first therapeutic agent may be stored at a concentration of 10 mg/mL and have normal dosing rates between 0.5 mg/hour and 1.5 mg/hour. A second therapeutic agent may be stored at a concentration of 100 mg/mL and have normal dosing rates of 25 mg/hour and 50 mg/hour. A y-axis scale appropriate for the first therapeutic agent, i.e., a scale that does not distort a graphical object representing a typical dosing regimen to be either too small or to extend beyond the display area of the display device, will not work for the second therapeutic agent without creating the distortion issues highlighted above.

The techniques of this disclosure relate to automatically determining an appropriate default scale for the y-axis based on an input therapeutic agent concentration. In particular, the techniques of this disclosure relate to a method of receiving, by a device for programming an implantable fluid delivery device, a therapeutic agent concentration, wherein the therapeutic agent concentration indicates a mass of a therapeutic agent per unit of volume of a fluid delivered by the implantable fluid delivery device. The techniques also comprise determining, by the device for programming the implantable fluid delivery device, a reference rate value based on the received therapeutic agent concentration, wherein the reference rate value comprises a mass per unit of time. The techniques further comprise displaying, with the device for programming the implantable fluid delivery device, a graphical user interface comprising a horizontal axis and a vertical axis, wherein the horizontal axis represents time and the vertical axis represents rates of delivery of the fluid by the implantable fluid delivery device, wherein a maximum value of the vertical axis displayed in the graphical user interface is determined based on the determined reference rate value, and wherein the maximum value of the displayed vertical axis is determined to be less than a maximum infusion rate.

FIG. 1 is a conceptual diagram illustrating an example of an implantable fluid delivery system 10, which includes IMD 12 configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. In one example, catheter 18 may comprise a plurality of catheter segments. In other examples, catheter 18 may comprise a unitary catheter. In the example of FIG. 1, the therapeutic agent is a therapeutic fluid. IMD 12 may comprise, for example, an implantable fluid delivery device that delivers therapeutic agents in fluid form to patient 16. In the example shown in FIG. 1, the target site is an intrathecal region proximate to spinal cord 14 of patient 16. A proximal end 18A of catheter 18 is coupled to IMD 12, while a distal end 18B of catheter 18 is located proximate to the target site. Implantable fluid delivery system 10 also includes external programmer 20, which wirelessly communicates with IMD 12 as needed, such as to provide or retrieve therapy information or control aspects of therapy delivery, e.g., modify therapy parameters, turn IMD 12 on or off, and so forth. While patient 16 is generally referred to as a human patient, other mammalian or non-mammalian patients are also contemplated.

IMD 12 may have an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

Catheter 18 may be coupled to IMD 12 either directly or with the aid of an extension. In the example shown in FIG. 1, catheter 18 traverses from the implant site of IMD 12 to one or more target sites proximate to spine 14. Catheter 18 is positioned such that one or more fluid delivery outlets of catheter 18 are proximate to one or more target sites within patient 16. IMD 12 delivers a therapeutic agent to one or more target sites proximate to spinal cord 14 with the aid of catheter 18. For example, IMD 12 may be configured for intrathecal drug delivery into an intrathecal space or epidural space surrounding spinal cord 14. The intrathecal space is within the subarachnoid space of spinal cord 14, which is past the epidural space and dura matter and through the theca of spinal cord 14.

Implantable fluid delivery system 10 may be used, for example, to reduce pain experienced by patient 16. IMD 12 may deliver one or more therapeutic agents to patient 16 according to one or more dosing programs that set forth different therapy parameters, such as a therapy schedule specifying programmed doses, dose rates for the programmed dose, and specific times to deliver the programmed doses. In some examples, the therapeutic agent may comprise a liquid. The dosing programs may comprise a part of a program group for therapy, where the group includes a plurality of therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. IMD 12 may further store one or more session histories in the memory. Patient 16 may select and/or generate additional dosing programs for use by IMD 12 via external programmer 20 at any time during therapy or as designated by the clinician. Patient 16 may, in accordance with the techniques of this disclosure, adjust the therapy parameters according to an infusion graph via a display device of implantable fluid delivery system 10.

In some examples, multiple catheters 18 may be coupled to IMD 12 to target the same or different tissue sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein.

Programmer 20 comprises an external computing device that is configured to wirelessly communicate with IMD 12. For example, programmer 20 may comprise a clinician programmer that the clinician uses to communicate with IMD 12. Alternatively, programmer 20 may comprise a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired changes to the operation of IMD 12.

Programmer 20 may comprise a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate through the user interface of programmer 20 and provide input.

If programmer 20 includes buttons and a keypad, the buttons may be dedicated to performing a certain function, i.e., a power button, or the buttons and the keypad may comprise soft keys that change in function depending upon the section of the user interface currently viewed by the user. Alternatively, the screen (not shown) of programmer 20 may comprise a touch screen that allows the user to provide input directly to the user interface shown on the display. The user may use a stylus or their finger to provide input to the display.

In other examples, rather than being a handheld computing device or a dedicated computing device, programmer 20 may comprise a larger workstation or a separate application within another multi-function device. For example, the multi-function device may comprise a cellular phone, personal computer, laptop, workstation computer, or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include system 10 hardware information such as the type of catheter 18, the position of catheter 18 within patient 16, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more dosing programs that define the therapy delivered by IMD 12. During a programming session, the clinician may determine one or more dosing programs that may provide effective therapy to patient 16. Patient 16 may provide feedback to the clinician as to the efficacy of a specific program being evaluated or desired modifications to the dosing program, e.g., via a patient programmer in communication with IMD 12. Once the clinician has identified one or more programs that may be beneficial to patient 16, patient 16 may continue the evaluation process and determine which dosing program or therapy schedule best alleviates the condition of patient 16 or otherwise provides efficacious therapy to patient 16.

According to some examples, programmer 20 and IMD 12 may be combined into a single device. For example, IMD 12 may not be implanted within patient 16. Rather, IMD 12 may connect to an implanted catheter 18, where a portion of catheter 18 extends external to the patient. In such examples, IMD 12 may incorporate one or more of the features described with respect to programmer 20. For example, IMD 12 may include a display device and one or more input mechanism that allows the user to navigate through the user interface of programmer 20 and provide input. A clinician, or, in some examples, patient 12 may program the IMD 12 via the display device. In at least one example, a clinician or patient 12 may program the IMD 12 according to an infusion graph displayed on the display device of IMD 12.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive patient-initiated boluses (e.g., a lock-out interval), a maximum dose that may be delivered over a given time interval, and so forth. IMD 12 may include a feature that prevents dosing the therapeutic agent in a manner inconsistent with the therapy program. Programmer 20 may assist the clinician in the creation or identification of therapy programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient should be limited to a maximum amount, such as a maximum daily dose, in order to avoid potential side effects. Program information specified by a user via programmer 20 may be used to control dosage amount, dosage rate, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate with IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

Programmer 20 may also include a user interface, such as a display, to display an infusion graph. For example, programmer 20 may display a graphical representation of a dosing program, including an x-axis and a y-axis. The x-axis may be broken into discrete time intervals, such as 10 minute intervals, 1 hour intervals, 1 day intervals, or the like. The y-axis may represent different therapeutic agent delivery rate values. In some examples, the rate may be expressed in units of mass per unit of time. For example, one set of common units used to express rate is milligrams per hour. Accordingly, a y-axis representing rates of milligrams per hour represents the amount of drug, in milligrams, that is delivered by system 10 per hour. It should be understood that other mass units and other time units may be used to express the rate. According to such a graphical representation of a dosing program, a clinician or patient 16 may easily see, in a graphical form, the total dose to be delivered to the patient. For instance, the infusion graph may include one or more graphical figures, such as a bar in a standard bar chart, that span one or more time intervals and correspond to various y-axis values. Accordingly, the area of the graphical figure, or the combined areas of a plurality of graphical figures, represents the total dose of the drug to the patient. A clinician or patient 16 may adjust the parameters of the displayed dosing program by adjusting the height and width of one or more graphical figures.

In accordance with techniques of this disclosure, programmer 20 may automatically determine a maximum value for the y-axis of a displayed infusion graph and display the infusion graph with a y-axis according to the determined maximum y-axis value. Selecting a maximum y-axis value for the displayed infusion graph helps to ensure easy programming and viewing of the dosing parameters by a clinician or patient 12. In some examples, programmer 20 may receive input comprising a therapeutic agent and a therapeutic agent concentration. The therapeutic agent concentration may be input as a mass per unit of volume, e.g., in milligrams per milliliters. Based on the received therapeutic agent concentration, programmer 20 may determine a reference rate value. The reference rate value may represent a particular dosing rate of the particular therapeutic agent to be delivered by system 10. For example, programmer 20 may determine a reference rate value based on the received therapeutic agent concentration. Programmer 20, in some instances, may further display an infusion graph and a y-axis according to the determined reference rate. For example, programmer 20 may display an infusion graph including a y-axis with a maximum y-axis value determined based on the determined reference rate value. In some examples, programmer 20 may determine more than one reference rate value. For example, in at least one example, programmer 20 may determine a first reference rate value and a second reference rate value. In other examples, other devices of system 10 separate from programmer 20 may automatically determine a scale for the y-axis. In other examples, programmer 20 may determine a reference rate value in conjunction with one or more other devices of system 10.

Intrathecal delivery was described above. In other applications of therapy system 10, the target therapy delivery site within patient 16 may be a location proximate to sacral nerves (e.g., the S2, S3, or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve.

As further examples, catheter 18 may be positioned to deliver a therapeutic agent to help manage peripheral neuropathy or post-operative pain mitigation, e.g., with respect to an ilioinguinal nerve or intercostal nerve, gastric therapy for the treatment of gastric motility disorders and obesity, or muscle spasticity or other movement disorders, for mitigation of other peripheral and localized pain (e.g., leg pain or back pain).

As another example, catheter 18 may be positioned to deliver a therapeutic agent to a deep brain site or within the heart (e.g., intraventricular delivery of the agent). Delivery of a therapeutic agent with the brain may help manage any number of disorders or diseases. Example disorders may include depression or other mood disorders, dementia, obsessive-compulsive disorder, migraines, obesity, and movement disorders, such as Parkinson's disease, Alzheimers' disease, spasticity, and epilepsy. Catheter 18 may also be positioned to deliver insulin to a patient with diabetes.

Examples of therapeutic agents that IMD 12 may be configured to deliver include, but are not limited to, insulin, morphine, other pain mitigating pharmaceutical agents, genetic agents, antibiotics, nutritional fluids, analgesics, hormones or hormonal drugs, gene therapy drugs, anticoagulants, proteins, growth factors, cardiovascular medications or chemotherapeutics.

Figure 2:
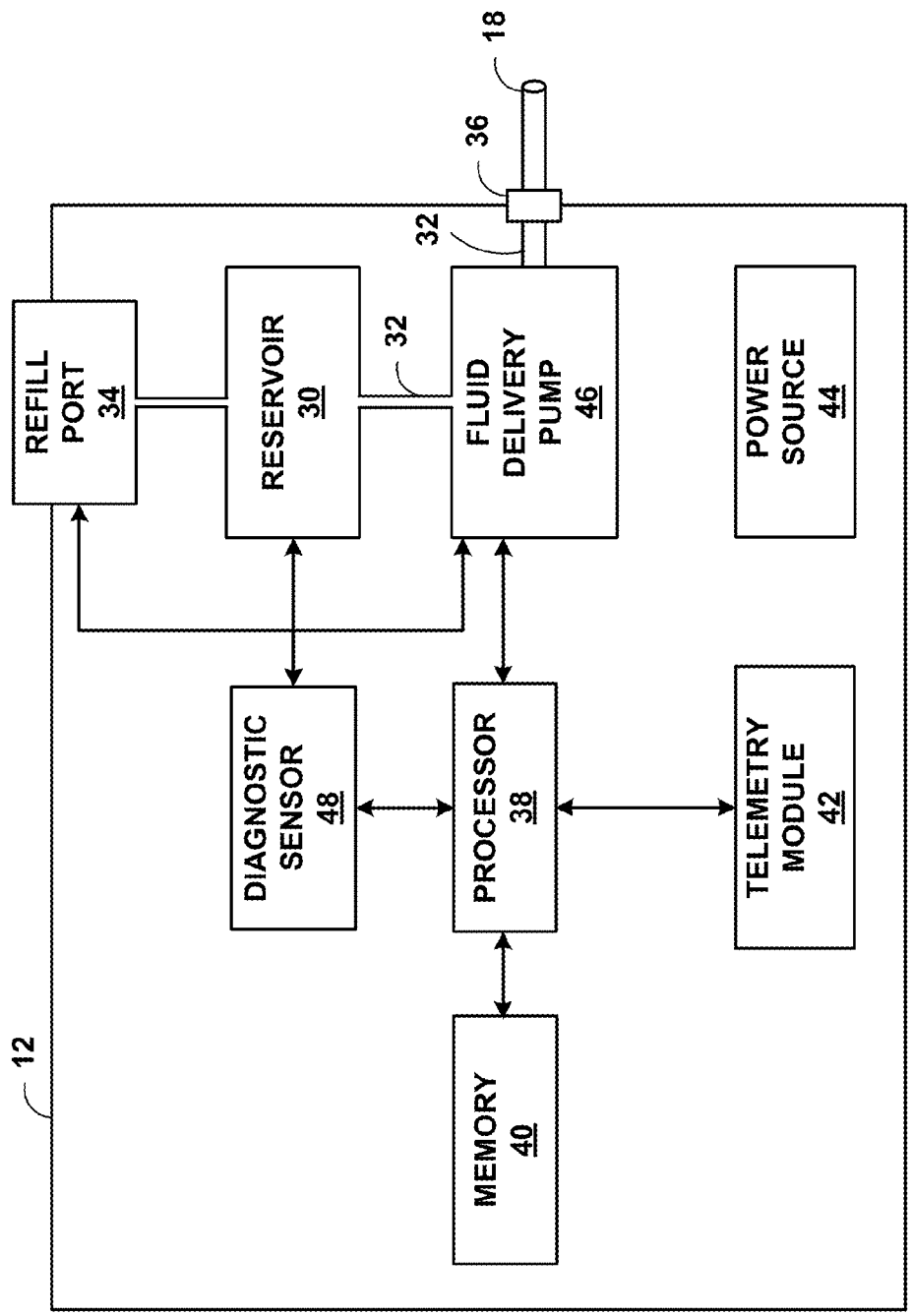
FIG. 2 is functional block diagram illustrating an example of an implantable fluid delivery device.

FIG. 2 is a functional block diagram illustrating components of an example of IMD 12, which includes refill port 34, reservoir 30, processor 38, memory 40, telemetry module 42, power source 44, fluid delivery pump 46, internal tubing 32, diagnostic sensor 48, and catheter access port 36. Fluid delivery pump 46 may comprise a mechanism that delivers a therapeutic agent in some metered or other desired flow dosage to the therapy site within patient 16 from reservoir 30 via the catheter 18. Refill port 34 may comprise a self-sealing membrane to prevent loss of therapeutic agent delivered to reservoir 30 via refill port 34. After a delivery system, e.g., a hypodermic needle, penetrates the membrane of refill port 34, the membrane may seal shut when the needle is removed from refill port 34.

Diagnostic sensor 48 may comprise means for detecting problems, changes, or interactions with one or more of the mechanisms of IMD 12 (for example, refill port 34, reservoir 30, fluid delivery pump 46, catheter access port 36, or catheter 18) or means for detecting clinical actions associated with one of the pump mechanisms (for example, to detect that reservoir 30 was accessed for refill, catheter 18 was accessed via port 36, reservoir 30 was filled/emptied, catheter 18 was revised or changed, etc.). The means for detecting problems, changes, or interactions with these components may comprise one or more pressure sensors. Diagnostic sensor 48 may send a signal to processor 38 upon detecting one or more of these problems, changes, or interactions with the components of IMD 12. In some examples, processor 38 may periodically issue a query to diagnostic sensor 48 to retrieve information collected by diagnostic sensor 48. Processor 38 may store information retrieved from diagnostic sensor 48 in memory 40. In some examples, processor 38 may record in memory 40 that a program revision was downloaded to IMD 12 in the middle of a therapy session, e.g., as a revision to a current dosing program.

In some examples, IMD 12 may have a sensing capability, e.g., diagnostic sensor 48, that can detect diagnostic conditions of the pump hardware and certain clinical actions performed on the pump system. This sensing capability may consist of a plurality of pressure sensors positioned in one or more locations in the fluid delivery path, including refill port 34, reservoir 30, catheter access port 36, fluid delivery pump 46, or a catheter connection. Diagnostic conditions checked by such a pressure sensing system may include the integrity of the catheter (patency, blockage, kinking, or other conditions preventing flow to the tip), the status of the pumping mechanism (missing or extra infusion based on stalls or other mechanical conditions), and the status of the reservoir (over or under pressure conditions). Clinical actions that can be detected based on such a pressure sensing system include insertion of a needle in one of the ports for purposes of refill or catheter access, reservoir filling or aspiration, and catheter connection or disconnection as in a revision surgery or replacement. Inclusion of such detected diagnostic conditions or clinical actions in a therapy session history may improve interpretation of such histories. For instance, a programmed pump priming activity in a case where no catheter aspiration was detected might help explain unexpected patient symptoms or non-optimal therapy outcomes.

Diagnostic sensor 48 may generally detect any or all of the conditions described above. Moreover, diagnostic sensor 48 may send a signal to processor 38 corresponding to the sensed diagnostic condition. Processor 38 may, in turn, store a representation of the sensed diagnostic condition in memory 40, e.g., as part of therapy session data for presentation to a user.

Internal tubing 32 is a segment of tubing that runs from reservoir 30, around or through fluid delivery pump 46, to catheter access port 36. In one example, fluid delivery pump 46 may comprise a squeeze pump that squeezes internal tubing 32 in a controlled manner, e.g., such as a peristaltic pump, to progressively move fluid from reservoir 30 to the distal end of catheter 18 and then into the patient according to parameters specified by a set of program information. Fluid delivery pump 46 may, in other examples, comprise an axial pump, a centrifugal pump, a pusher plate, a piston-driven pump, or other means for moving fluid through internal tubing 32 and catheter 18.

Processor 38 controls the operation of fluid delivery pump 46, e.g., by executing instructions associated with dosing program information stored in memory 40. For example, the instructions may define therapy schedules of a dosing program that each specify the rate at which a therapeutic fluid is to be delivered to a target tissue site within patient 16 from reservoir 30 via catheter 18. The instructions may further specify the time at which the fluid will be delivered and the time interval over which the agent will be delivered at that rate. The amount of the fluid to be delivered is a function of the dosage rate at which the fluid is delivered and the time over which the rate is to be applied. The instructions may be encoded in memory 40, which may comprise a computer-readable storage medium such as, for example, a hard drive or a solid state medium such as a flash drive or memory chip, as described with respect to various examples in greater detail below. In some examples, the computer-readable storage medium is a non-transitory storage medium. The term "non-transitory" may indicate that the storage medium is not embodied in a carrier wave or a propagated signal. However, the term "non-transitory" should not be interpreted to mean the storage medium is non-movable.

Fluid delivery pump 36 may have a range of possible fluid pump rates. That is, fluid delivery pump 36 may be able to deliver fluid at varying rates, e.g., rates at which fluid delivery pump 36 can pump fluid, but the range may have an upper and a lower bound representing the minimum and maximum fluid pump rates for fluid delivery pump 36. The maximum and minimum fluid pump rates may be affected by the particular implementation of fluid delivery pump 36, such as the design of a motor used to pump the fluid or the circuitry controlling the motor. In some examples, fluid delivery pump 36 may have a minimum pump rate that is greater than zero. In other examples, fluid delivery pump 36 may have a minimum pump rate of zero.

However, users, such as physicians may prefer to think in terms of therapeutic agent infusion rates, which is the amount of therapeutic agent pumped by IMD 12 into a patient, rather than the amount of fluid pumped by fluid delivery pump 36 and delivered to a patient. Since therapeutic agents may be stored in IMD 12 at different concentrations, differing amounts of therapeutic agents may be delivered to a patient even at a same fluid pump rate. For example, if a first therapeutic agent is stored in IMD 12 at a concentration of ten milligrams per milliliter (10 mg/mL), and fluid delivery pump 36 is configured to pump one milliliter of fluid per hour (1 mL/hr), the therapeutic agent infusion rate would be ten milligrams per hour (10 mg/hr). In another example, if a second therapeutic agent is stored in IMD 12 at five hundred milligrams per milliliter (500 mg/mL), and fluid delivery pump 36 is configured to pump at one milliliter of fluid per hour (1 mL/hr), the therapeutic agent infusion rate would be five hundred milligrams per hour (500 mg/hr).

As fluid delivery pump 36 may have maximum and minimum fluid pump rates, IMD 12 may have maximum and minimum therapeutic agent infusion rates. In some examples, the maximum and minimum therapeutic agent infusion rates are based both on the maximum and minimum fluid pump rates of fluid delivery pump 36 of IMD 12 and the concentration of the therapeutic agent to be delivered by IMD 12. For example, if IMD 12 has a maximum fluid pump rate of twenty four milliliters per day (24 mL/day or 1 mL/hr), and a therapeutic agent stored at ten milligrams per milliliter (10 mg/mL), the maximum therapeutic agent infusion rate for IMD 12 is ten milligrams per hour (10 mg/hr). In other examples, the maximum and minimum therapeutic agent infusion rates may bet set based on factors other than the mechanical limits of IMD 12, such as by a user (e.g., a patient or a physician) or a manufacturer. For example, a user may set maximum and minimum therapeutic agent infusion rates in order to provide increased patient safety by not allowing a patient to adjust the therapeutic agent infusion rate to be too high or too low for safe and effective therapy. In other examples, a manufacturer may set maximum and minimum therapeutic agent infusion rates, as IMD 12 may be physically capable of achieving higher or lower therapeutic agent infusion rates, achieving those rates may damage IMD 12. In still other examples, maximum and minimum therapeutic agent infusion rates may be determined by IMD 12 based on the received therapeutic agent. For example, IMD 12 may store maximum and minimum therapeutic agent infusion rates associated with specific therapeutic agents in memory 40. Accordingly, after receiving an indication of a therapeutic agent, IMD 12 may retrieve from memory 40 the maximum and minimum therapeutic agent infusion rates associated with that specific therapeutic agent.

In some examples, the maximum and minimum fluid pump rates for IMD 12 may be stored in memory 40. After receiving a therapeutic agent concentration, processor 38 may then retrieve the maximum and minimum fluid pump rates from memory 40 and determine maximum and minimum therapeutic agent infusion rates. In other examples, memory 40 may store a table of maximum and minimum therapeutic agent infusion rates based on concentration. In such examples, after receiving a therapeutic agent concentration, processor 38 may retrieve the corresponding maximum and minimum therapeutic agent infusion rates from the table stored in memory 40.

The dosing program may also include other therapy parameters, such as a plurality of therapy schedules, the type of therapeutic agent delivered (if IMD 12 is configured to deliver more than one type of therapeutic agent), concentrations of a drug or drugs in a therapeutic fluid, and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, dosing programs, historical dosing programs, timing programs for delivery of fluid from reservoir 30 to catheter 18, and any other information regarding therapy of patient 16. A therapy schedule may indicate the bolus size or flow rate of the drug, and processor 38 may accordingly deliver therapy.

Memory 40 may include separate memories for storing instructions, patient information, therapy parameters, therapy adjustment information, program histories, and other categories of information such as any other data that may benefit from separate physical memory modules or separate memory units. Therapy adjustment information may include information relating to timing, frequency, rates, and amounts of fluid doses or other permitted patient modifications to therapy. In some examples, memory 40 stores program instructions that, when executed by processor 38, cause IMD 12 and processor 38 to perform the functions attributed to them in this disclosure.

Memory 40 may, in some examples, store therapy session information including data relating to a plurality of therapy sessions. When IMD 12 is reprogrammed by programmer 20, all or a portion of a current dosing program may be retained in memory 40 as a historical therapy session. During a therapy session, IMD 12 may record data related to the therapy session in memory 40, such as patient feedback (e.g., related to efficacy of the dosing program), patient-requested supplemental boluses, whether IMD 12 delivered a supplemental bolus in response to the patient's request, clinician notes or comments, or other data.

Telemetry module 42 in IMD 12, as well as telemetry modules in other devices described herein, such as programmer 20, may accomplish communication by RF communication techniques. In addition, telemetry module 42 may communicate with programmer 20 via proximal inductive interaction of IMD 12 with external programmer 20. Accordingly, telemetry module 42 may send information to external programmer 20 on a continuous basis, at periodic intervals, or upon request from the programmer. Processor 38 controls telemetry module 42 to send and receive information. Wireless telemetry may be accomplished by RF communication or proximal inductive interaction of IMD 12 with external programmer 20. In some examples, programmer 20 may retrieve session history information from IMD 12 or download session history information to IMD 12 via telemetry module 42. Telemetry module 42 may also receive signals from a patient programmer device for patient requests for supplemental boluses. Telemetry module 42 may also receive signals from the patient programmer device regarding patient feedback for a current therapy session.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Figure 3:
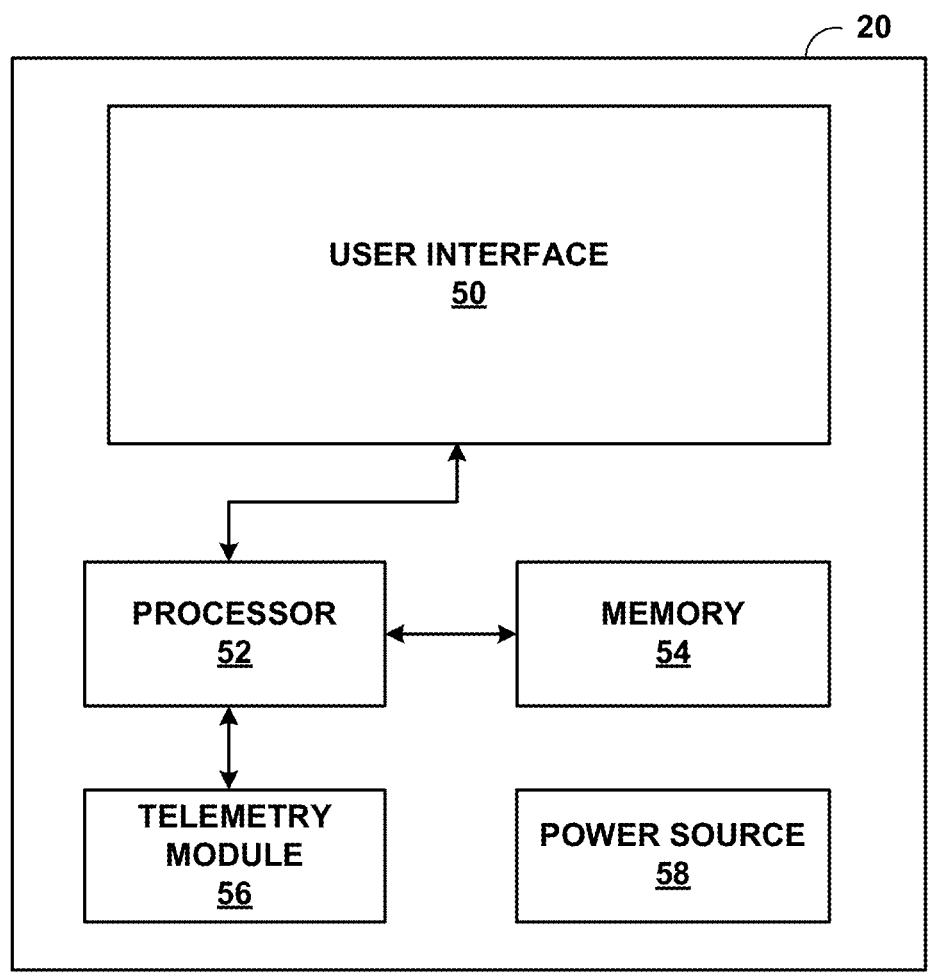
FIG. 3 is a functional block diagram illustrating components of an external programmer for an implantable medical device.

FIG. 3 is a functional block diagram illustrating various components of an external programmer 20 for IMD 12. As shown in FIG. 3, external programmer 20 includes processor 52, memory 54, telemetry module 56, user interface 50, and power source 58. A clinician or patient 16 interacts with user interface 50 in order to manually change the parameters of a dosing program, change dosing programs within a group of programs, view therapy information, view historical therapy regimens, establish new therapy regimens, or otherwise communicate with IMD 12 or view programming information.

User interface 50 may include a screen and one or more input buttons, as discussed in greater detail below, that allow external programmer 20 to receive input from a user. Alternatively, user interface 50 may additionally or only utilize a touch screen display. The screen may comprise a liquid crystal display (LCD), dot matrix display, organic light-emitting diode (OLED) display, touch screen, or any other device capable of delivering and/or accepting information.

Input buttons for user interface 50 may include a touch pad, increase and decrease buttons, emergency shut off button, and other buttons needed to control the therapy, as described above with regard to patient programmer 20. Processor 52 controls user interface 50, retrieves data from memory 54 and stores data within memory 54. Processor 52 also controls the transmission of data through telemetry module 56 to IMD 12. Memory 54 includes operation instructions for processor 52 and data related to patient therapy. That is, memory 54 may be encoded with executable instructions, and processor 52 may be configured to execute the instructions.

In some examples, interface 50 may comprise a touch-sensitive display. In such examples, users may provide input directly to interface 50. The user may use a stylus or their finger to provide input to the display. As described previously, the user may input dosing parameters, types of therapeutic agents, therapeutic agent concentrations, dosing programs, or any other input described herein.

User interface 50 may be configured to present therapy program information to the user. User interface 50 enables a user to program IMD 12 in accordance with one or more dosing programs, therapy schedules, or the like. As discussed in greater detail below, a user such as a clinician, physician or other caregiver may input patient information, drug information, therapy schedules, priming information, bridging information, drug/IMD implant location information, or other information to programmer 20 via user interface 50. In addition, user interface 50 may display therapy program information as bar graphs or charts, numerical spread sheets, or in any other manner in which information may be displayed. Further, user interface 50 may present nominal or suggested therapy parameters that the user may accept via user interface 50. In this manner, user interface 50 may display a graphical representation of a dosing program, one example of which may be described herein as an infusion graph, to be administered by the implantable fluid delivery device.

Processor 52 may receive user input from user interface 50. Alternatively, in some instances, user input is stored in memory 54 and processor 52 receives user input from memory 54. Specifically, processor 52 may receive input comprising therapeutic agent concentration. In some examples, processor 52 may also receive maximum and minimum fluid pump rates of IMD 12. For example, processor 52 may receive the maximum and minimum fluid pump rates from memory 54 or from another device, such as IMD 12 in conjunction with telemetry module 56. Based on the received therapeutic agent concentration and the received maximum and minimum fluid pump rates, processor 52 may determine maximum and minimum therapeutic agent infusion rates. In other examples, processor 52 may receive maximum and minimum therapeutic agent infusion rates directly from memory 54 or from another device, such as IMD 12 in conjunction with telemetry module 56.

Processor 52 may further determine a reference rate value based on the received therapeutic agent concentration. For example, processor 52 may determine a reference rate value including a mass value that is a particular percent of the mass value of the therapeutic agent concentration. In at least one example, processor 52 may be configured to determine a reference rate value that includes a mass value that is ten percent of the mass value of the received therapeutic agent concentration. The reference rate value may represent a therapeutic agent infusion rate, and, in some examples, processor 52 may cause user interface 50 to display an infusion graph representing a dosing program according to the reference rate value. As described previously, an infusion graph may be a graph including an x-axis that is broken into discrete time units and a y-axis that represents therapeutic agent infusion rates, which may be described throughout this disclosure as simply y-axis "rates" or "rate values."

Processor 52 may cause user interface 50 to display an infusion graph including y-axis rate values that range from the minimum infusion rate to the maximum infusion rate. However, in some instances, it may be beneficial to display the infusion graph wherein the maximum and minimum y-axis values are different from the maximum and minimum therapeutic agent infusion rates. In particular, it may be beneficial to display an infusion graph where the maximum y-axis value is less than the maximum therapeutic agent infusion rate. For example, in some instances, processor 52 may cause user interface 50 to display the infusion graph including various graphical objects which represent a dosing program. In these examples, the height of the graphical objects may correspond to a y-axis value and represent a therapeutic agent infusion rate at which IMD 12 delivers a therapeutic agent to a patient. Additionally, the width of the graphical object may represent a time period over which IMD 12 delivers the therapeutic agent at the specified therapeutic agent infusion rate. In some examples, the height of graphical objects of a dosing program may correspond to y-axis therapeutic agent infusion rate values that are less than the maximum therapeutic agent infusion rate of IMD 12. In such instances, the displayed graphical objects may be relatively small in proportion to the overall infusion graph. Users may encounter difficulty interacting with graphical objects that are small relative to the infusion graph. Accordingly, some of the techniques of the present disclosure relate to automatically determining a reference rate value that is less than the maximum therapeutic agent infusion rate. The techniques further describe automatically displaying an infusion graph with a maximum y-axis value corresponding to the reference rate value.

Displaying a dosing program as an infusion graph may assist a user to easily visually determine the dosing parameters (the rate of therapeutic agent infusion and the amount of time of therapeutic agent infusion) and even adjust the dosing parameters. Additionally, processor 52 may be configured to cause user interface 50 to display the y-axis at a certain scale according to the reference rate value. For example, processor 52 may be configured to cause user interface 50 to display the y-axis with a maximum y-axis value determined based on the determined reference rate value. In some examples, processor 52 may be configured to cause user interface 50 to display a y-axis with a maximum y-axis value that is the determined reference rate value.

Telemetry module 56 allows the transfer of data to and from IMD 12. Telemetry module 56 may communicate automatically with IMD 12 at a scheduled time or when the telemetry module detects the proximity of IMD 12. Alternatively, telemetry module 56 may communicate with IMD 12 when signaled by a user through user interface 50. To support RF communication, telemetry module 56 may include appropriate electronic components, such as amplifiers, filters, mixers, encoders, decoders, and the like. Power source 58 may comprise a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12. Communicated data described by this disclosure may be communicated between IMD 12, programmer 20, and the recharging device via any type of external device capable of communication with IMD 12.

In this manner, external programmer 20 is an example of a programmer device that receives therapeutic agent concentration input, wherein the therapeutic agent concentration comprises a mass per unit of volume and a processor that determines a reference rate value based on the received therapeutic agent concentration, wherein the reference rate value comprises a mass per unit of time. Programmer 20 is also an example of a programmer device that displays a graphical interface comprising an x-axis and a y-axis, wherein the maximum y-axis value of the displayed y-axis is determined based on the determine reference rate value, and wherein the maximum value of the displayed vertical axis is determined to be less than a maximum infusion rate.

Figure 4A:
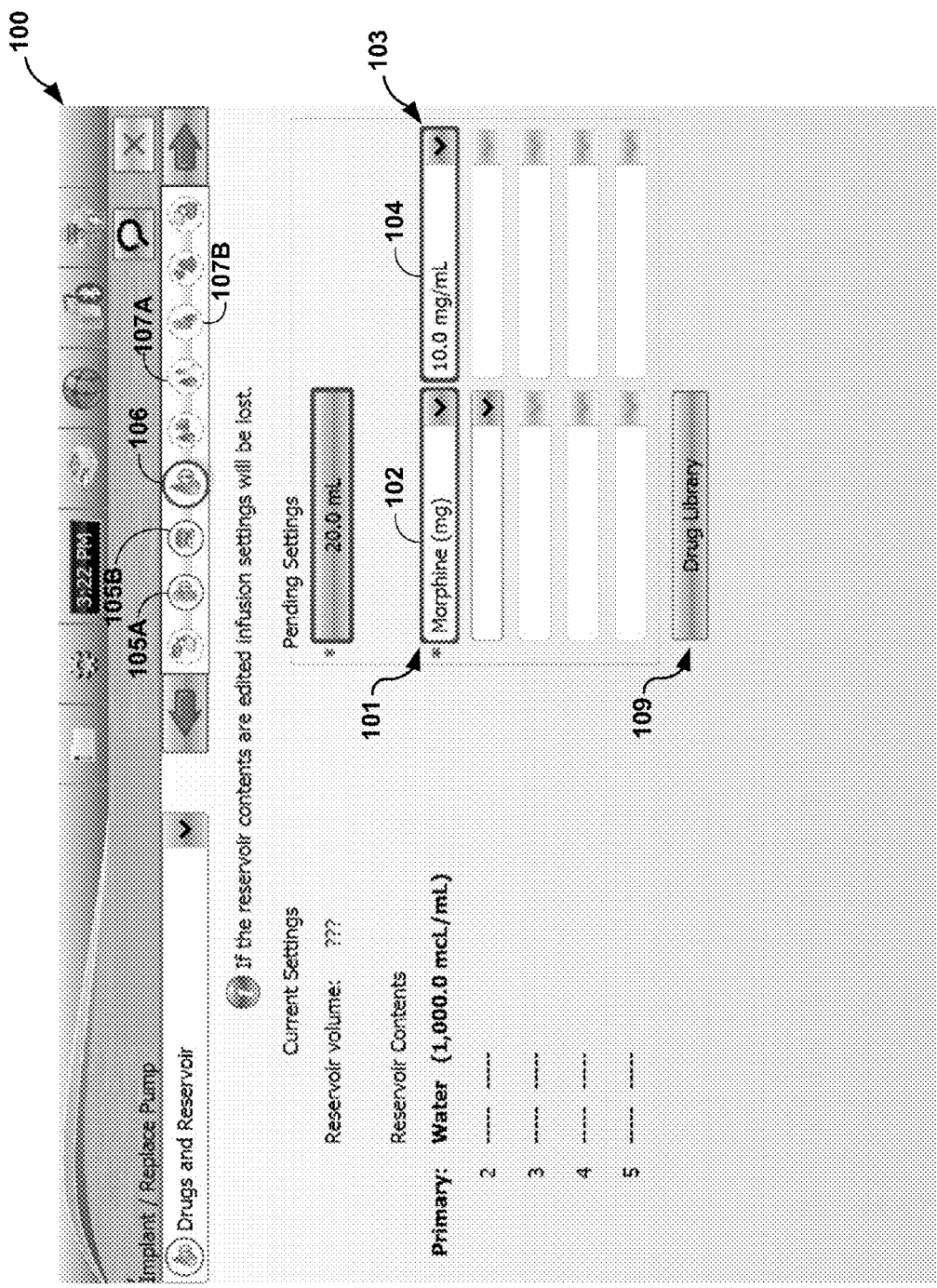
FIG. 4A is a screenshot illustrating an example graphical interface screen presented by an external programmer for selecting a therapeutic agent and therapeutic agent concentration values.
Figure 4B:
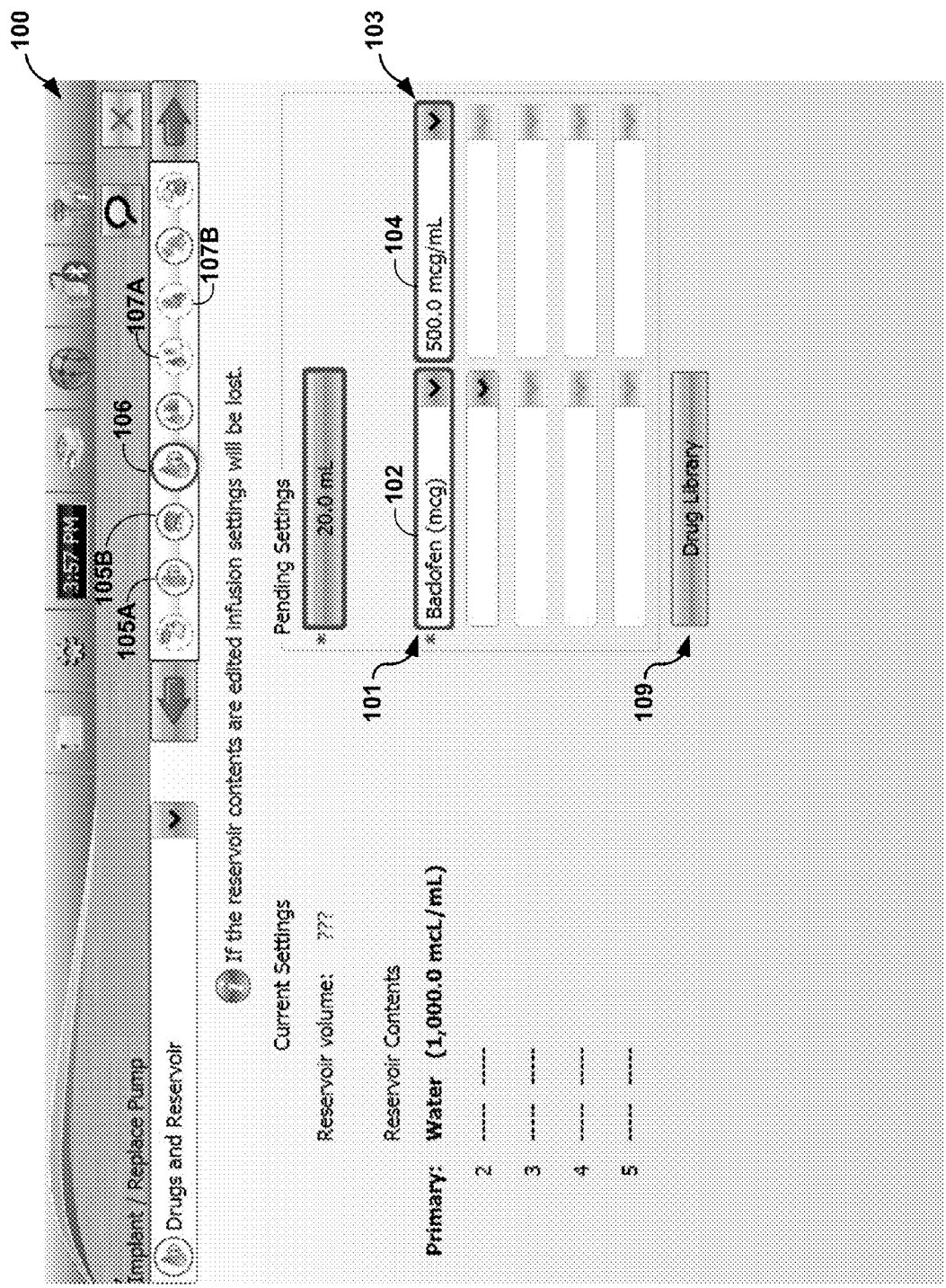
FIG. 4B is a screenshot illustrating an example graphical interface screen presented by an external programmer for selecting a therapeutic agent and therapeutic agent concentration values.

FIGS. 4A and 4B are screenshots illustrating an example user interface screen 100 presented by programmer 20 for selecting a therapeutic agent and therapeutic agent concentration values. User interface screen 100 may be displayed by user interface 50 of programmer 20. At some point during interaction with programmer 20, programmer 20 presents user interface screen 100 to the user. User interface screen 100 may be one of multiple user interface screens that a user may select to display. A user may select other user interface screens to display by selecting elements 105A or 105B or any other similar elements depicted in FIGS. 4A and 4B with a solid green border. Other user interface screens which a user may not currently select to display are represented by elements 107A and 107B and the other elements depicted in FIGS. 4A and 4B with grey dashed borders. Element 106, which is slightly larger relative to the other elements and includes a thicker green border represents the active user interface screen. That is, by selecting element 106, programmer device may present a user with user interface screen 100.

The user may also enter drug information into drug selection area 101 and concentration selection area 103. The user may select a drug from a drop-down menu of drug selection area 101 that is to be delivered to reservoir 30 of IMD 12. The user may also select a corresponding concentration of the drug from a corresponding drop-down menu of concentration selection area 103. Example drugs that may be listed by drop-down menus of drug selection area 101 include saline (as a default filler or as a placebo during clinical testing or other drug trails), morphine, bupivacaine, clonidine, hydromorphone, baclofen, alpha adrenergic agonists, baclofen, fentanyl, sufentanil, ziconotide, or other drugs or fluids. Selecting drugs from multiple drop-down menus of drug selection area 101 indicates that a combination of drugs is to be delivered to reservoir 30. For example, a user may select "morphine" from a first drop-down menu and "bupivacaine" from a second drop-down menu of drug selection area 101. When IMD 12 has already been programmed according to a dosing program with a first fluid, i.e., a fluid containing a drug at a particular concentration, user interface screen 100 displays the first drug and the first concentration of the drug. If the user changes the drug, processor 52 may recognize the fact that the drug and/or concentration has changed and may cause user interface screen 100 to suggest that a bridge be performed.

The user may also select Drug Library 109 to link to a drug library. User interface screen 100 may then display a list of drugs and information regarding each of the listed drugs, such as names of the drugs, one or more common concentration values, and units for the values. In one example, the user may select a drug from the drug library, including a concentration of the drug, and user interface screen 100 populates one or more of drop-down menus 101 and/or 103 with the user's selection. In one example, the user may select a drug from the drug library, including a concentration of the drug, and user interface screen 100 populates one or more of drop-down menus 101 and/or 103 with the user's selection. In one example, the drug library may be user definable, allowing a user to enter names of drugs, one or more concentrations that are used for the drugs, and units for the concentrations.

Within user interface screen 100, the user may provide input comprising a selection of a particular therapeutic agent 102 from a list of therapeutic agents. Therapeutic agent 102 may be configured for different mass units. For example, by receiving a selection of a therapeutic agent with a particular mass unit, programmer 20 may be configured to express other values, such as therapeutic agent concentration 104 or a therapeutic agent infusion rate in the selected mass unit or based on the selected mass unit. As depicted in FIG. 4A, in at least one example, therapeutic agent 102 may comprise morphine and may be expressed in terms of milligrams (mg). Additionally, within user interface screen 100, the user may provide input comprising a selection of a particular therapeutic agent concentration 104. Generally, therapeutic agent concentration 104 represents the concentration at which therapeutic agent 102 is stored within implantable fluid delivery system 10. As depicted in FIG. 4A, one example therapeutic agent concentration 104 is ten milligrams per milliliter (10 mg/mL). FIG. 4B depicts input comprising a different selection of therapeutic agent 102 and a different selection of therapeutic agent concentration 104. Specifically, FIG. 4B depicts selection of therapeutic agent 102 baclofen expressed in micrograms (mcg). Additionally, FIG. 4B depicts selection of therapeutic agent concentration 104 of five hundred micrograms per milliliter (500.0 mcg/mL).

In one example, processor 52 determines, from therapeutic agent concentration 104, a reference rate value that includes a mass value that is ten percent of the mass value of therapeutic agent concentration 104. As described previously, processor 52 may receive the input directly from user interface 50 or indirectly from user interface 50 via memory 54. In the example of FIG. 4A, processor 52 may determine a reference rate value that includes a mass value of one milligram (1 mg). In the example of FIG. 4B, processor 52 may determine a reference rate value that includes a mass value of fifty micrograms (50 mcg). Additionally, therapeutic agent concentration may determine a time period for the reference rate value. For example, processor 52 may determine a time period of one hour. Accordingly, processor 52 may determine reference rate values of one milligram per hour (1 mg/hr) and fifty micrograms per hour (50 mcg/hr) in the examples of FIGS. 4A and 4B, respectively. In some examples, processor 52 may determine a time period different than one hour, such as one minute, ten minutes, thirty minutes, six hours, twelve hours, one day, one week, one month, or any other time period.

Processor 52 may determine other reference rate values that include mass values that are varying percents of the received therapeutic agent concentration. For example, processor 52 may determine one or more reference rate values that include mass values that are between approximately two-tenths of a percent (0.2%) and approximately twenty percent (20%) of the mass value of the received therapeutic agent concentration. In some examples, processor 52 may determine one or more reference rate values that include mass values that are approximately two-tenths of a percent (0.2%), two and a half percent (2.5%), five percent (5%), ten percent (10%), fifteen percent (15%), and twenty percent (20%) of the mass value of the received therapeutic agent concentration. In the example of FIG. 4A, the determined mass values may range from two-one hundredths milligrams (0.02 mg) to two milligrams (2 mg), such as two-one hundredths milligrams (0.02 mg), one-quarter milligrams (0.25 mg), one-half milligrams (0.5 mg), one milligram (1 mg), one and a half milligrams (1.5 mg), and two milligrams (2 mg). In the example of FIG. 4B, the determined mass values may range from one microgram (1 mcg) to one hundred micrograms (100 mcg), such as one microgram (1 mcg), twelve and a half micrograms (12.5 mcg), twenty five micrograms (25 mcg), fifty micrograms (50 mcg), seventy-five micrograms (75 mcg), and one hundred micrograms (100 mcg). Again, processor 52 may determine a time period associated with each of the determined mass values to create the one or more reference rate values, as described previously.

In some examples, processor 52 may automatically select one of the one or more reference rate values as the determined reference rate value. For example, processor 52 may receive, e.g., from memory 54, percent values associated with particular therapeutic agents, and select the reference rate value corresponding to the received percent value as the determined reference rate value. As one illustrative example, processor 52 may receive a therapeutic agent concentration of Morphine at ten milligrams per milliliter (10 mg/mL). Processor 52 may generate one or more reference rate values including mass values that are varying percents of the mass value of the received concentration, e.g., 10 mg/mL. Additionally, processor 52 may receive from memory a percent value of ten percent (10%) associated with the therapeutic agent Morphine. Accordingly, processor 52 may then select the generated reference rate value of one milligram per hour (1 mg/hr), as one milligram is ten percent (10%) of the mass value of ten milligrams (10 mg) of the Morphine concentration, as the determined reference rate value. In other example, processor 52 may cause user interface device 50 to present to a user in a graphical user interface the one or more generated reference rate values. In such examples, a user may then select one of the displayed reference rate values as the determined reference rate value.

Figure 5A:
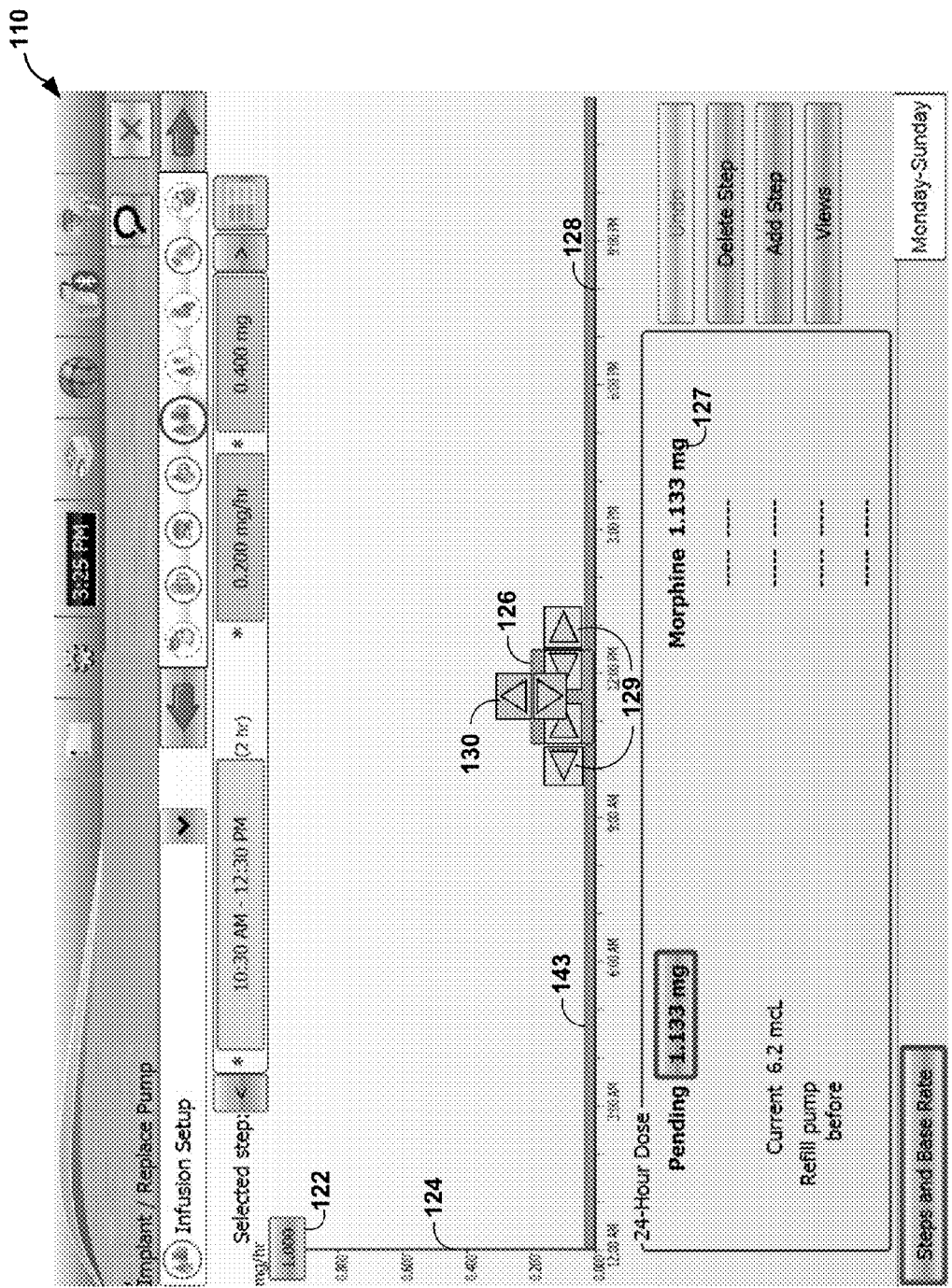
FIG. 5A is a screenshot illustrating an example graphical interface screen presented by an external programmer for displaying a current dosing program and configuring a new dosing program.
Figure 6A:
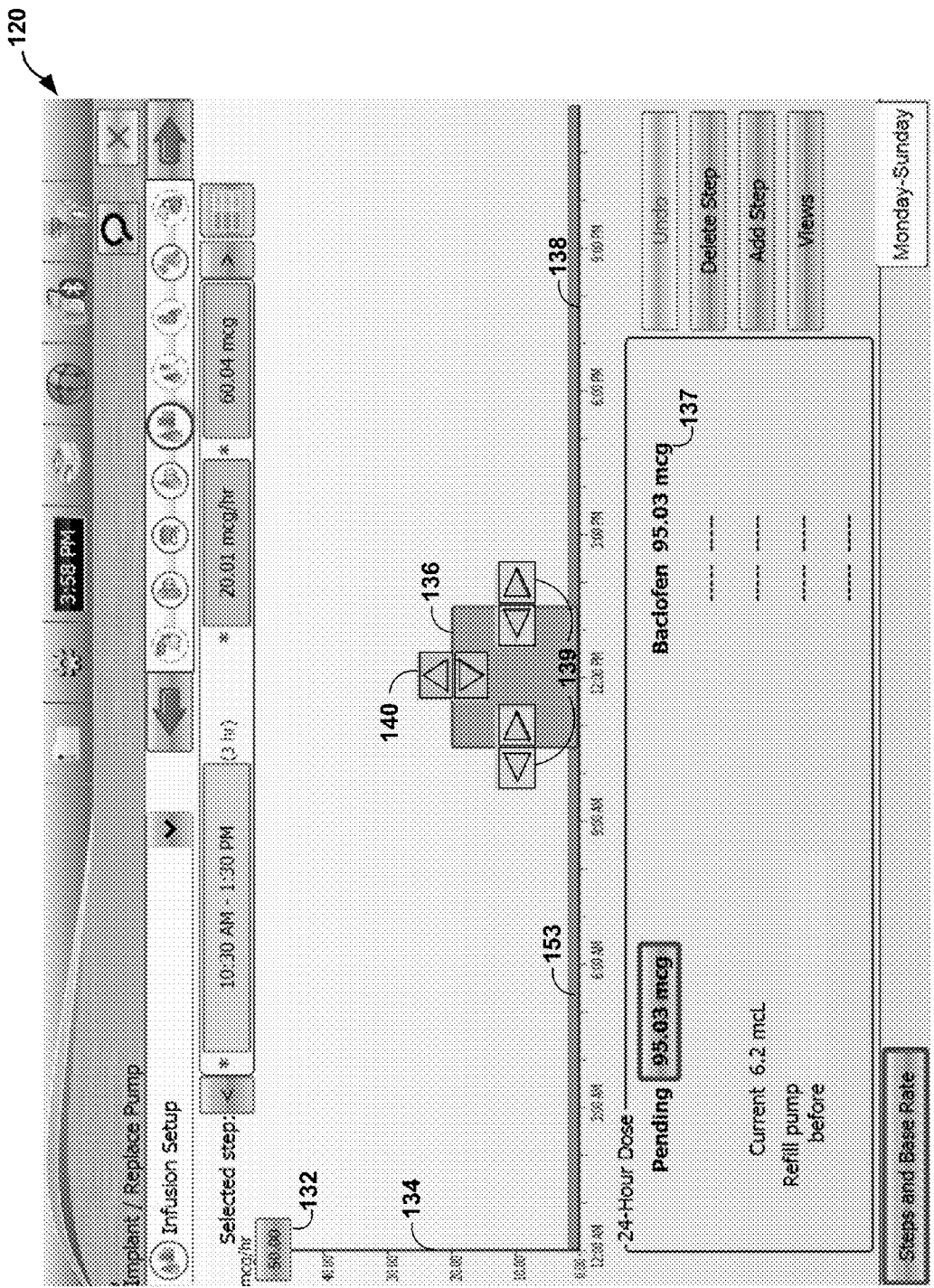
FIG. 6A is a screenshot illustrating an example graphical interface screen presented by an external programmer for displaying a current dosing program and configuring a new dosing program.

FIGS. 5A and 6A are screenshots illustrating an example user interface for displaying a current dosing program. FIGS. 5A and 6A are related to the screenshots illustrated in FIGS. 4A and 4B, with FIG. 5A relating to FIG. 4A and FIG. 6A relating to FIG. 4B. For example, FIGS. 5A and 6A display dosing programs according to the therapeutic agent and therapeutic agent concentrations selections depicted in FIGS. 4A and 4B. The example infusion pattern of FIGS. 5A and 6A include graphical objects 126 and 136, respectively, indicating a dosing rate and a time period. For example, according to graphical objects 126 and 136, programmer 20 may pump a therapeutic agent at an infusion rate indicated by a y-axis 124 value corresponding to the top portions of graphical objects 126 and 136 and for a time period corresponding to the width of the bases of graphical objects 126 and 136 relative to x-axis 128. For example, according to FIG. 5A, programmer 20 is programmed to deliver morphine, indicated by therapeutic agent text 127, at a rate of two-tenths of a milligram per hour (0.2 mg/hr) between the hours of 10:30 am and 12:30 pm. In the example of FIG. 6A, programmer 20 is programmed to deliver baclofen, indicated by therapeutic agent text 137, at a rate of twenty and one one-hundredth micrograms per hour (20.01 mcg/hr) between the hours of 10:30 am and 12:30 pm.

A user may select one or more of dose adjustment buttons 129 or 130 in FIG. 5A, or dose adjustment buttons 139 or 140 in FIG. 6A, in order to adjust graphical FIG. 126 or 136, respectively. For example, if a user selects dose adjustment button 129 in FIG. 5A, or dose adjustment button 139 in FIG. 6A, the user may select a first one of the arrows of the button to expand the base of graphical object 126 or 136 or the second one of the arrows of the button to contract the base of graphical object 126 or 136. Expanding the base of graphical object 126 or 136 increases the total programmed dose to be delivered by programmer 20 because it programs programmer 20 to deliver the therapeutic agent indicated by therapeutic agent text 127 or 137 for a longer period of time. Contracting the base of graphical object 126 or 136 has the opposite effect, namely decreasing the programmed dose to be delivered by programming programmer 20 to deliver the therapeutic agent for a shorter period of time. Alternatively, a user may select dose adjustment button 130 in FIG. 5A or dose adjustment button 140 in FIG. 6A. Selecting a first arrow of dose adjustment button 130 or 140 may increase the height of graphical object 126 or 136. Selecting a second arrow of dose adjustment button 130 or 140 may decrease the height of graphical object 126 or 136. Increasing the height may increase the total dose programmed to be delivered by programmer 20 because it programs programmer 20 to deliver the therapeutic agent at a higher rate over a same period of time. Conversely, decreasing the height may decrease the total dose programmed to be delivered by programmer 20 because it programs programmer 20 to deliver the therapeutic agent at a lower rate over a same period of time. Accordingly, before adjustment, the top portion of graphical objects 126 and 136 may correspond to a first y-axis rate value. After adjustment, the top portions of graphical objects 126 and 136 may correspond to a second y-axis rate value.

Processor 52 may cause user interface 50 to display user interface screen 110 or 120 of FIGS. 5A and 6A, respectively. User interface screen 110 includes y-axis 124 and x-axis 128, and user interface screen 120 includes y-axis 134 and x-axis 138. Additionally, processor 52 may cause user interface 50 to display user interface screen 110 or 120 according to the determined reference rate values. For example, in FIG. 4A, a user input a therapeutic agent concentration of ten milligrams per milliliter (10 mg/mL), and in FIG. 4B, a user input a therapeutic agent concentration of five hundred micrograms per milliliter (500 mcg/mL). In FIGS. 5A and 6A, processor 52 may be configured to determined reference rate values that include a mass unit that is ten percent (10%) of the mass value of the therapeutic agent concentration. Accordingly, in the examples of FIGS. 5A and 6A, processor 52 may determine reference rate values of one milligram per hour (1 mg/hr) and fifty micrograms per hour (50 mcg/hr).

In the examples of FIGS. 5A and 6A, processor 52 causes user interface 50 to display user interface screens 110 and 120 including maximum y-axis rate 122 and maximum y-axis rate 132 determined based on the determined reference rate values. In the examples of FIGS. 5A and 6A, processor 52 determined the maximum y-axis values to be the determined reference rate values. In other examples, processor 52 may determine the maximum y-axis values to be a fraction or a multiple of the determined reference rate value. For example, in FIG. 5A, processor 52 causes user interface 50 to display user interface screen 110 with maximum y-axis rate 122 of one milligram per hour (1 mg/hr). In the example of FIG. 6A, processor 52 causes user interface 50 to display user interface screen 120 with maximum y-axis rate 132 of fifty micrograms per hour (50 mcg/hr). Additionally, processor 52 may cause user interface 50 to display user interface screens 110 and 120 with y-axis rates ranging from zero to the determined reference rate values and broken into segments with each segment representing twenty percent, forty percent, sixty percent, and eighty percent of maximum y-axis rate 122 or maximum y-axis rate 132. These ranges of displayed values may be collectively termed a y-axis scale. In other examples, processor 52 may determine a maximum y-axis value Additionally, in other examples, processor 52 may determine one or more reference rate values that includes a mass value that is between approximately two-tenths (0.2%) of a percent and approximately twenty percent (20%) of the mass value of the received therapeutic agent concentration, or in other examples, approximately two-tenths of a percent (0.2%), two and a half percent (2.5%), five percent 5%), ten percent (10%), fifteen percent (15%), and twenty percent (20%) of the mass value of the therapeutic agent concentration. Accordingly, processor 52 may further determine a maximum y-axis value based on these one or more reference rate values.

Determining and displaying a scale, e.g., the range of values of the y-axis, is important in assisting a user in being able to select dose adjustment buttons 129 and 130 or dose adjustment buttons 139 and 140 and visualize and compare graphical objects 136 and 146. For example, if a user selects a dosing program including at least one graphical object 126 or 136, depending on the dosing parameters embodied by graphical object 126 or 136, the displayed object may either be small relative to the infusion graph or the top of the object may not even be displayed because the y-axis rate corresponding to the top of graphical object 126 or 136 may be beyond y-axis maximum rate 122 or y-axis maximum rate 132. If the top of the object is not displayed, a user may not be able to easily adjust the height of the object and thereby not be able to easily adjust the dosing rate by selecting dose adjustment button 130 or dose adjustment button 140. Alternatively, if graphical object 126 or 136 is too small, a user may have difficulty selecting the proper dose adjustment button 129 or 139, or more specifically the first or second arrows of either dose adjustment button. Accordingly, a user may encounter difficulty in adjusting the length of time programmer 20 is programmed to deliver the therapeutic agent. Additionally, if the graphical objects are small enough, a user may have trouble even seeing the graphical objects or comparing one graphical object to another graphical object. In such instances, a user may overlook important information about the dosing program. In this manner, determining and displaying user interface screen 110 or 120 with a maximum y-axis value according to a determined reference rate value as described herein assists programmer 20 in presenting users with a user interface screen that is easy to read and provides for easy interaction with the various dose adjustment buttons.

FIGS. 5A and 6A also include residual infusion rate elements 143 and 153. Residual infusion rate elements 143 and 153 may correspond to rate values and represent residual infusion rates at which IMD 12 delivers a therapeutic agent to a patient. A residual infusion rate may be, for example, an infusion rate at which IMD 12 delivers a therapeutic agent during time periods not associated with graphical elements. In FIGS. 5A and 6A, residual infusion rate elements 143 and 153 correspond to y-axis rate values. Accordingly, in the time periods before and after graphical objects 126 and 136, e.g. between 12:00 am and 10:30 am and between 12:30 pm and 11:59 pm, IMD 12 may deliver a therapeutic agent to a patient at the infusion rate corresponding to residual infusion rate elements 143 and 153. During the time periods associated with graphical elements 126 and 136, IMD 12 may deliver a therapeutic agent at an infusion rate corresponding to the height of graphical objects 126 and 136. In some examples, a user may select residual infusion rate elements 143 and 153. In these examples, after receiving input comprising a selection of residual infusion rate element 143 or 153, processor 52 may cause user interface 50 to display one or more additional elements (not shown) which a user may select to adjust residual infusion rate elements 143 and 153 up or down, thereby increasing or decreasing the residual infusion rate of the dosing program.

Figure 5B:
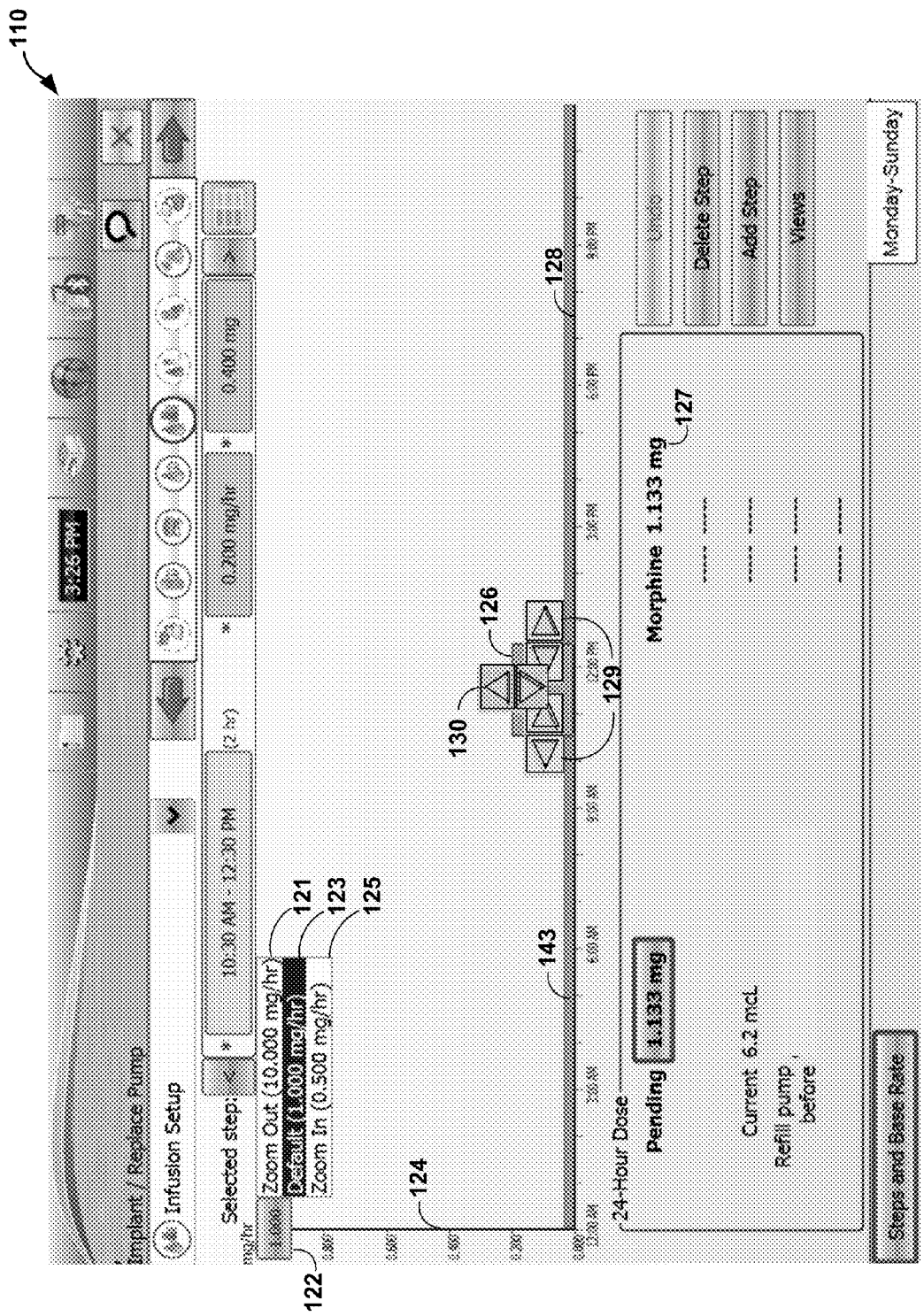
FIG. 5B is a screenshot illustrating an example graphical interface screen presented by an external programmer for adjusting the maximum value of the displayed vertical axis of the current dosing program.
Figure 6B:
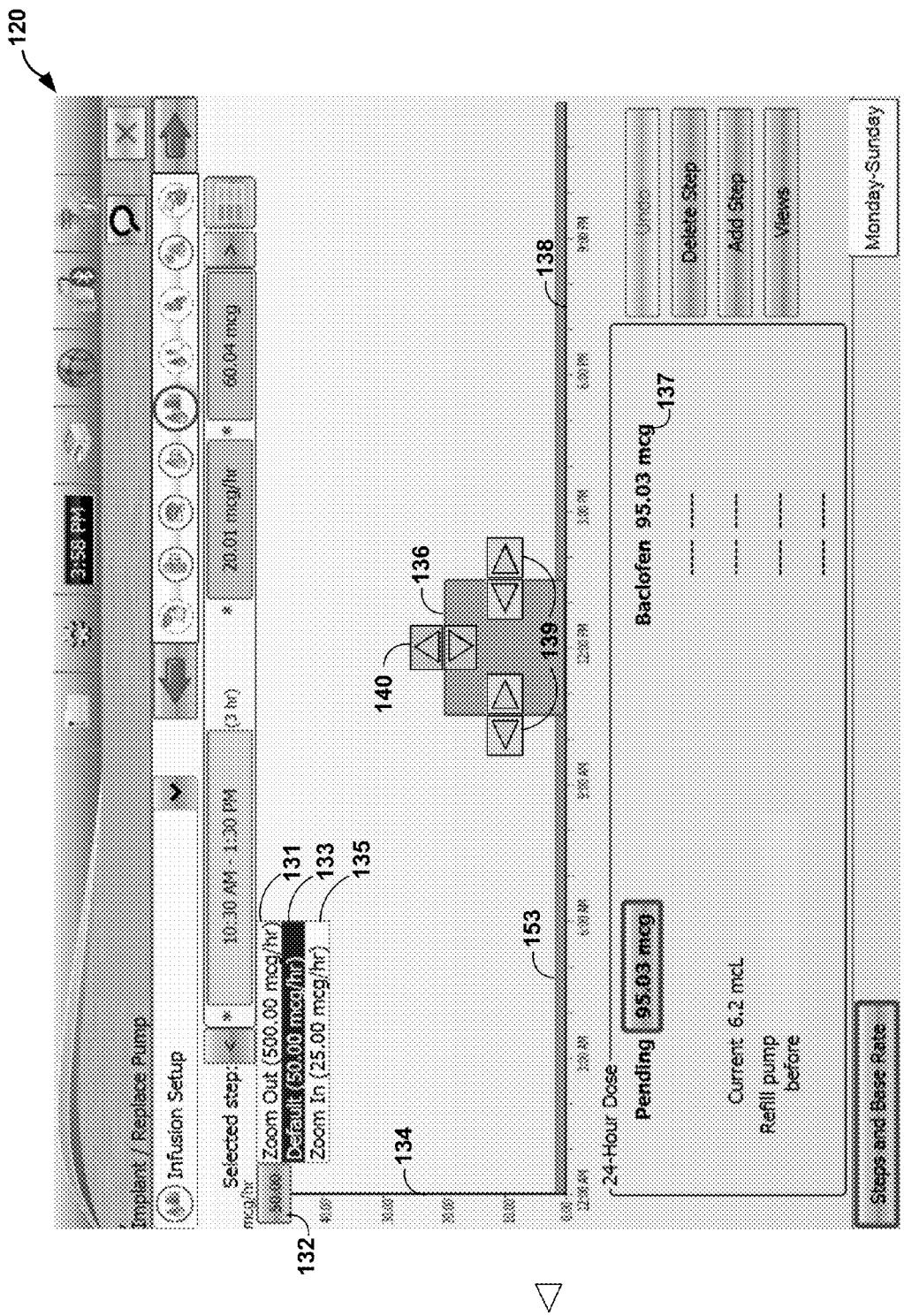
FIG. 6B is a screenshot illustrating an example graphical interface screen presented by an external programmer for adjusting the scale of the displayed vertical axis of the current dosing program.

FIGS. 5B and 6B are screenshots illustrating an example user interface presented by an external programmer for adjusting the maximum value of the displayed vertical axis of the current dosing program. In some examples, maximum y-axis rate 122, in FIG. 5B, or maximum y-axis rate 132, in FIG. 6B, is an element which a user may select. FIGS. 5B and 6B depict user interface screens 110 and 120 after a user has selected maximum y-axis value element 122 or maximum y-axis value element 132, respectively. Upon selection, processor 52 may cause user interface 50 to display user interface screen 110 or 120 including one or more zoom values, such as zoom values 121, 123, 125 in FIG. 5B or zoom values 131, 133, or 135 in FIG. 6B. The zoom values represent different maximum y-axis values and selecting one of the zoom values 121, 123, 125 or 131, 133, 135 may cause processor 52 to cause user interface 50 to display user interface screen 110 or 120 including an infusion graph representing the current dosing program with a different maximum y-axis value according to the selected zoom value. That is, processor 52 may cause user interface 50 to display user interface screen 110 or 120 including the y-axis with a new maximum y-axis value corresponding to the selected zoom value. Processor 52 may further cause user interface 50 to display user interface screen 110 or 120 including the y-axis according to the new maximum y-axis value.

In some examples, processor 52 may cause user interface 50 to display user interface screen 110 or 120 including three zoom values upon receiving a selection of maximum y-axis value element 122 or maximum y-axis value element 132. In at least one example, the three zoom values represent the current maximum y-axis value, a y-axis value including a mass value that is five percent (5%) of the mass value of the received therapeutic agent concentration, and a y-axis value including a mass value that is one hundred percent (100%) of the mass value of the received therapeutic agent concentration. In other examples, processor 52 may cause user interface 50 to display user interface screen 110 or 120 including additional zoom values or zoom values including mass values that are different percents of the mass value of the received therapeutic agent concentration. For example, processor 52 may cause user interface 50 to display user interface screen 110 or 120 including zoom values that include mass values that range between approximately two-tenths of a percent (0.2%) and approximately twenty percent (20%) of the mass value of the received therapeutic agent concentration. In other examples, processor 52 may cause user interface 50 to display user interface screen 110 or 120 including zoom values that include mass values that are approximately two-tenths of a percent (0.2%), two and a half percent (2.5%), five percent (5%), ten percent (10%), fifteen percent (15%), twenty (20%), fifty percent (50%), seventy five percent (75%), one hundred percent (100%), one hundred twenty five percent (125%), one hundred and fifty percent (150%), and two hundred percent (200%) of the mass value of the therapeutic agent concentration. In other examples, processor 52 may determine one or more zoom values according to a logarithmic or other nonlinear function in conjunction with the therapeutic agent concentration. In still other examples, processor 52 may determine one or more zoom values based on the determined reference rate value, e.g. such as determining one or more zoom values which are various fractions or multiples of the determined reference rate value.

According to the example of FIG. 5B, processor 52 may cause user interface 50 to display user interface screen 110 including zoom value 121 of ten milligrams per hr (10 mg/hr), zoom value 123 of one milligram per hour (1 mg/hr), and zoom value 125 of one-half milligram per hour (0.5 mg/hr). Zoom value 123 represents current maximum y-axis value 122. Upon receiving a selection of any of zoom values 121, 123, or 125, processor 52 may determine the selected zoom value to be new maximum y-axis value 122, or in the case that a user selects zoom value 123, no change may be made to maximum y-axis value 122. Based on new maximum y-axis value 122, processor 52 may cause user interface 50 to display user interface screen 110 including updated graphical object 126. For example, if a user selects a zoom value representing a smaller rate value than current maximum y-axis value 122, processor 52 may cause user interface 50 to display graphical object 126 with a greater height, or, alternatively, if a user selects a zoom value representing a larger rate value than current maximum y-axis value 122, processor 52 may cause user interface 50 to display graphical object 126 with a lesser height. As with graphical object 126, when adjusting the maximum y-axis value, processor 50 may also cause user interface 50 to display residual infusion rate element 143 with differing heights. That is, if the maximum y-axis value is increased, the size of residual infusion rate element 143 may be reduced and if the maximum y-axis value is decreased, the size of residual infusion rate element 143 may be increased. Accordingly, by selecting various zoom values, a user may adjust the height of graphical object 126. Adjusting the height of graphical object 126 may assist a user in selecting one or more of dose adjustment buttons 129 or 130 or in visualizing or any displayed graphical objects, such as graphical object 136. FIG. 6B represents similar user interface screen 120 including three different zoom values. FIG. 6B is substantially similar to FIG. 5B except for the type of drug and the maximum y-axis value and the zoom values. Accordingly, the description above with respect to FIG. 5B applies as well to FIG. 6B.

In other examples, processor 52 may cause user interface 50 to display user interface screen 110 or 120 after receiving a selection of maximum y-axis value element 122 or maximum y-axis value element 132 including zoom values which include mass value that are varying percents of current maximum y-axis value 122 or current maximum y-axis value 132. For example, processor 52 may determine one or more rate values that include mass values that are between approximately two-tenths of a percent (0.2%) and approximately two hundred percent (200%) of current maximum y-axis value 122. In some examples, processor 52 may determine one or more rate values that include mass values that are two-tenths of a percent (0.2%), two and a half percent (2.5%), five percent (5%), ten percent (10%), fifteen percent (15%), twenty percent (20%), fifty percent (50%), seventy five percent (75%), one hundred percent (100%), one hundred twenty five percent (125%), one hundred and fifty percent (150%), and two hundred percent (200%) of the mass value of current maximum y-axis rate 122. Accordingly, processor 52 may cause user interface 50 to display user interface screen 110 including determined rate values that are varying percents of current maximum y-axis rate 122 instead of varying percents of the received therapeutic agent concentration. In other examples, the displayed zoom values may include mass values that are varying percents, such as the percent values described above, of the mass value of the therapeutic agent concentration. Accordingly, processor 52 may display zoom values determined based on either the determined reference rate value or the received therapeutic agent concentration.

In still other examples, processor 52 may cause user interface 50 to display user interface screen 110 or 120 after receiving a selection of maximum y-axis value element 122 or maximum y-axis value element 132 including a text input box. A user may enter a number in the text input box where the number represents a percent value. The percent value may indicate a value by which to scale the current display. For example, upon receiving input comprising a percent value, processor 52 may determine a reference rate value that includes a mass value that is the received percent value of the received therapeutic agent concentration. Processor 52 may further cause user interface device 50 to display user interface 110 or 120 with a maximum y-axis value based on the determined reference rate value. Again, in some examples, the maximum y-axis value may be the determined reference rate value.

Figure 7:
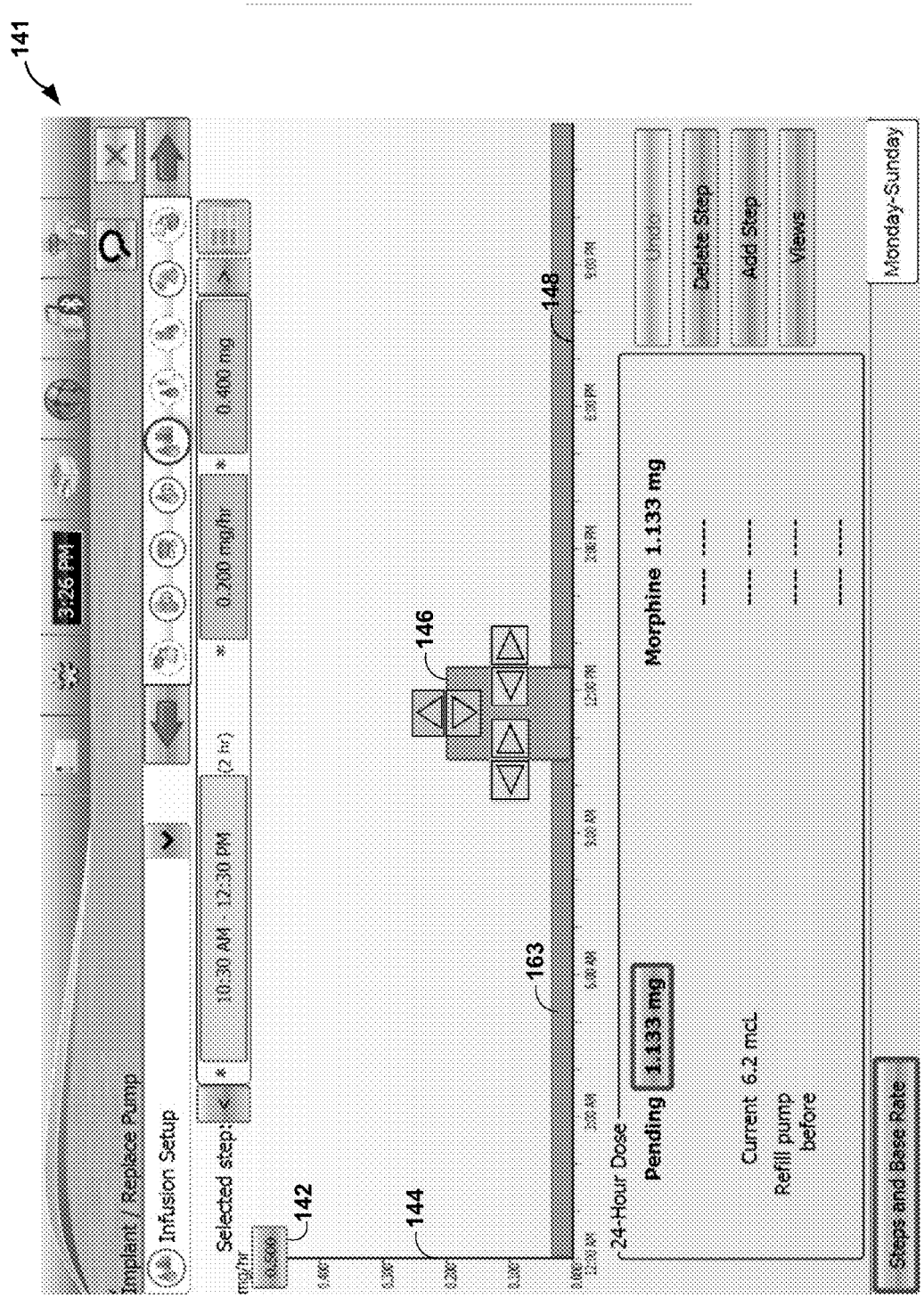
FIG. 7 is a screenshot illustrating an example graphical interface screen presented by an external programmer for displaying a current dosing program.
Figure 8:
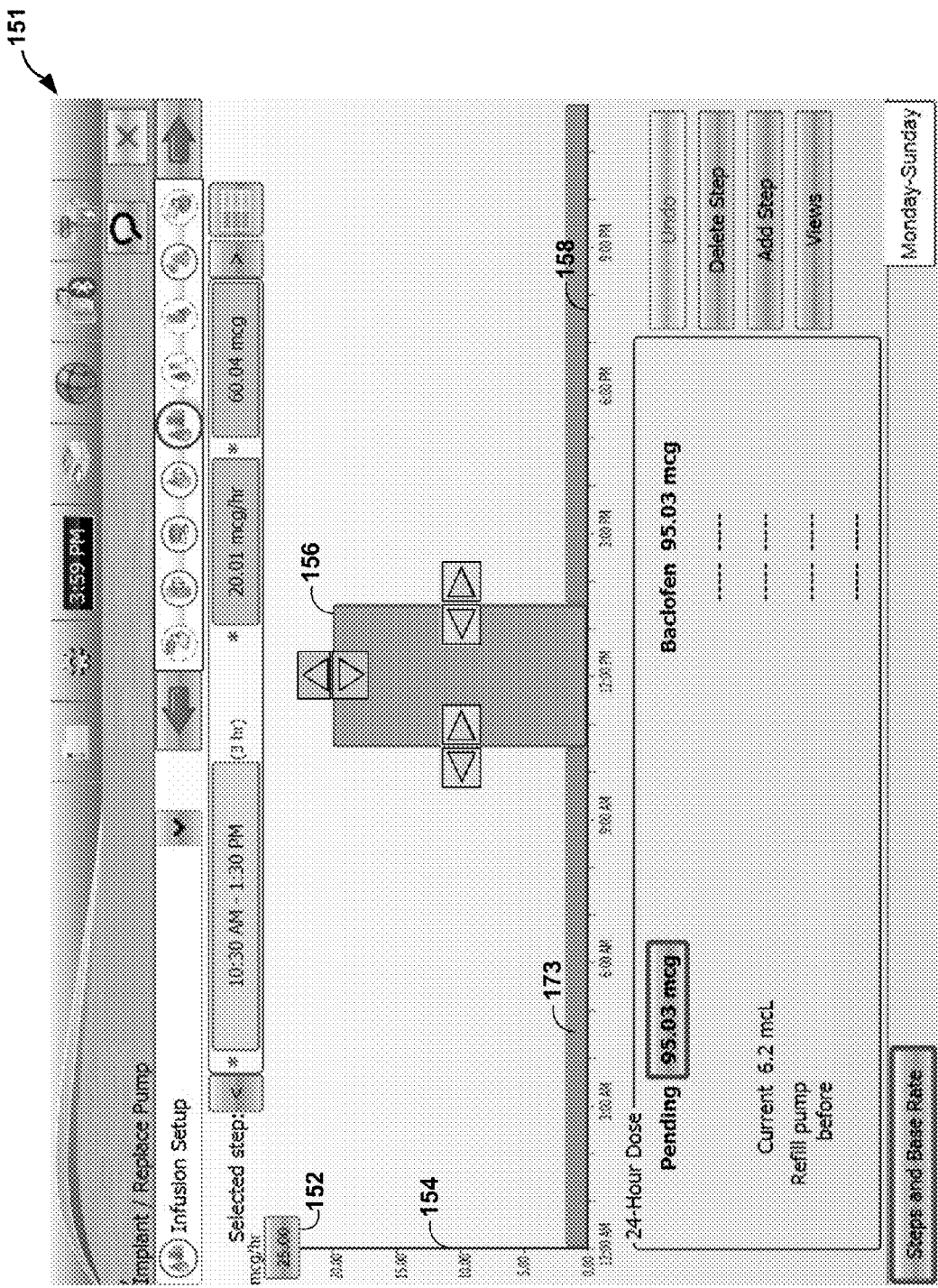
FIG. 8 is a screenshot illustrating an example graphical interface screen presented by an external programmer for displaying a current dosing program.

FIGS. 7 and 8 are screenshots illustrating example user interfaces presented by an external programmer for displaying a current dosing program. FIG. 7 depicts user interface screen 141 including y-axis 144, maximum y-axis value 142, graphical object 146, residual infusion rate element 163, and x-axis 148. FIG. 8 depicts user interface screen 151 including y-axis 154, maximum y-axis value 152, graphical object 156, residual infusion rate element 173, and x-axis 158. In the example of FIG. 7, maximum y-axis value 142 is one-half milligram per hour (0.5 mg/hr). Note that this maximum y-axis value is the same as zoom value 125 in FIG. 5B. Accordingly, FIG. 7 depicts user interface screen 141 which is an example of user interface screen 110 of FIG. 5B that has been scaled according to a new maximum y-axis value. Note the relative size increase between graphical object 126 and graphical object 146 and residual infusion rate elements 143 and 163. As described above with respect to FIG. 5B, upon receiving a selection of a smaller maximum y-axis value than a current y-axis value, processor 52 may cause user interface 50 to display a graphical object present in the dosing program, or a residual infusion rate element present in the dosing program, with a greater height. For example, FIG. 5B depicts graphical object 126 and a first maximum y-axis value (1.000 mg/hr), and FIG. 7 depicts graphical object 146, which is similar to graphical object 126 except with a greater height, and a second, smaller maximum y-axis value (0.500 mg/hr). FIG. 8 depicts graphical object 156 with a greater height relative to that of graphical object 136 of FIG. 6B. For example, FIG. 6B depicts graphical object 136 and a first maximum y-axis value (50.00 mg/hr), and FIG. 8 depicts graphical object 156, which is similar to graphical object 136 except with a greater height, and a second, smaller maximum y-axis value (25.00 mg/hr).

Figure 9:
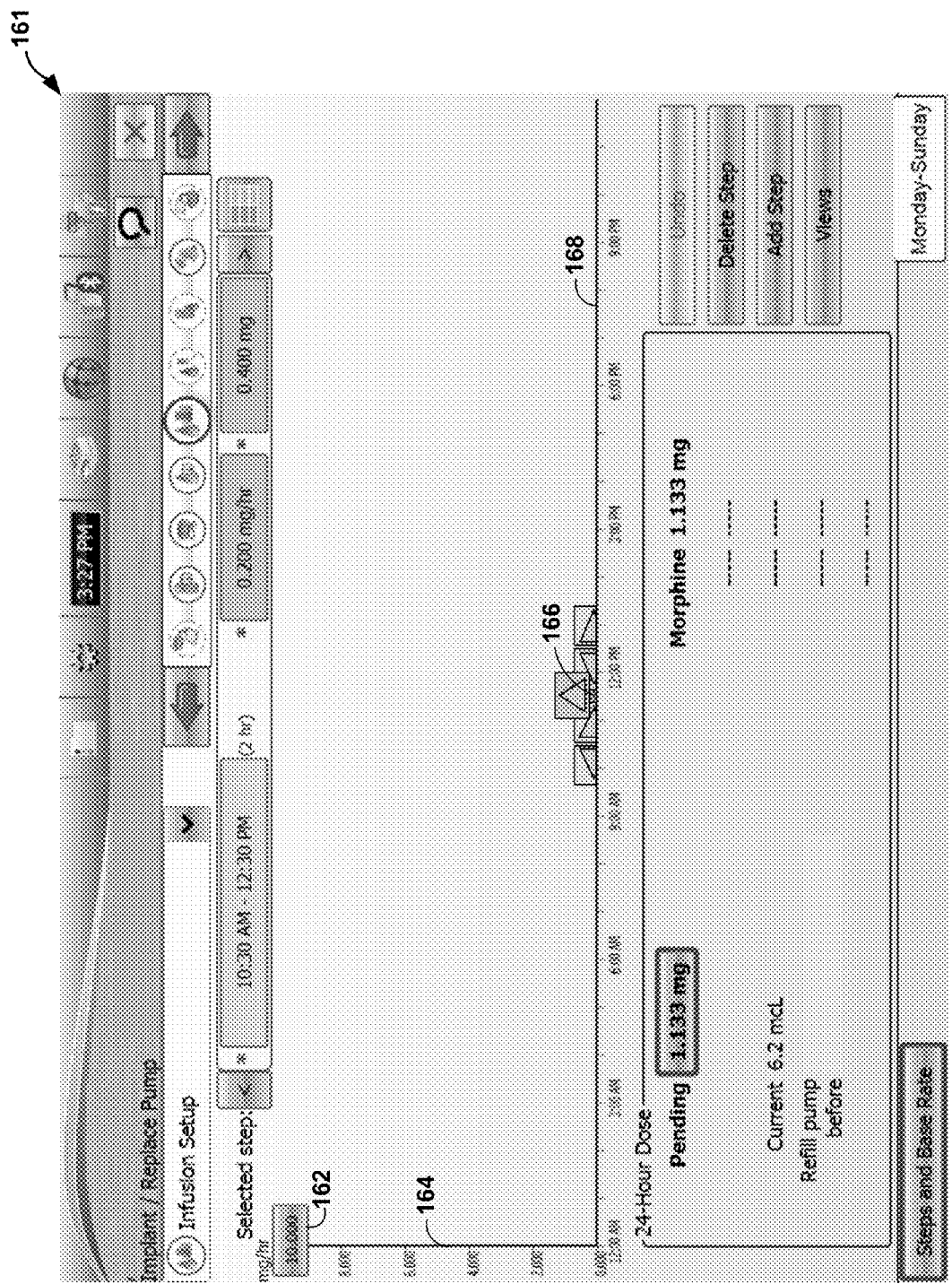
FIG. 9 is a screenshot illustrating an example graphical interface screen presented by an external programmer for displaying a current dosing program.
Figure 10:
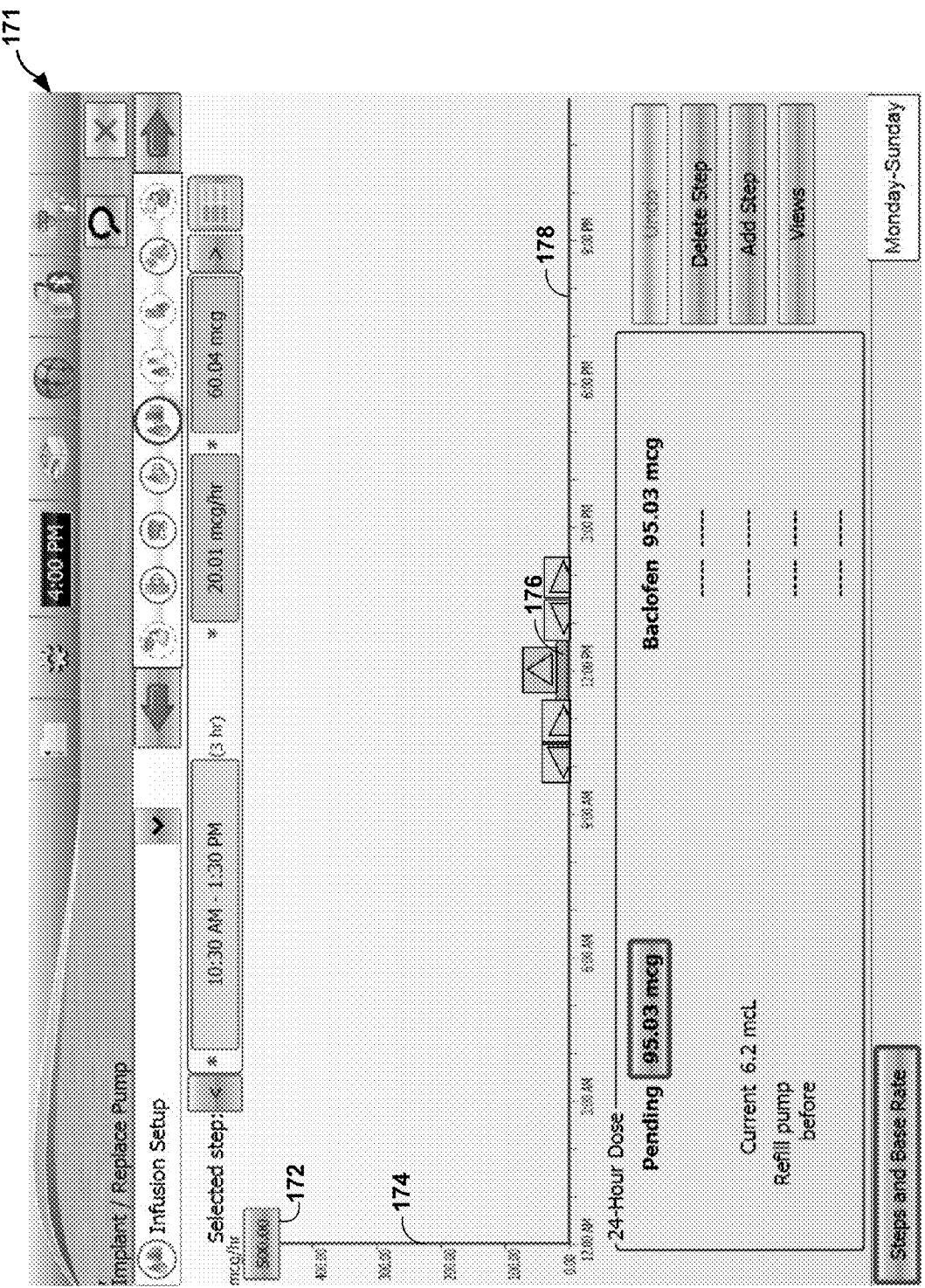
FIG. 10 is a screenshot illustrating an example graphical interface screen presented by an external programmer for displaying a current dosing program.

FIGS. 9 and 10 are screenshots illustrating example user interfaces which may be shown to a user by an implantable fluid delivery system. FIG. 9 depicts user interface screen 161 including y-axis 164, maximum y-axis value 162, graphical object 166, and x-axis 168. FIG. 8 depicts user interface screen 171 including y-axis 174, maximum y-axis value 172, graphical object 176, and x-axis 178. In the example of FIG. 9, maximum y-axis value 162 is ten milligrams per hour (10 mg/hr). Note that this maximum y-axis value is the same as zoom value 121 in FIG. 6B. Accordingly, FIG. 9 depicts user interface screen 161 which is an example of user interface screen 110 of FIG. 6B that has been scaled according to a new maximum y-axis value. Note the relative size decrease between graphical object 126 and graphical object 166. As described above with respect to FIG. 6B, upon receiving a selection of a larger maximum y-axis value than a current maximum y-axis value, processor 52 may cause user interface 50 to display a graphical object present with a lesser height. For example, FIG. 5B depicts graphical object 126 and a first maximum y-axis value (1.000 mg/hr, and FIG. 9 depicts graphical object 166, which is similar to graphical object 126 except with a lesser height, and a second, larger maximum y-axis value (10.000 mg/hr). FIG. 10 depicts graphical object 176 with a lesser height relative to that of graphical object 136 of FIG. 6B. For example, FIG. 6B depicts graphical object 136 and a first maximum y-axis value (50.00 mg/hr), and FIG. 10 depicts graphical object 176, which is similar to graphical object 136 except with a lesser height, and a second, larger maximum y-axis value (500.00 mg/hr).

Figure 11:
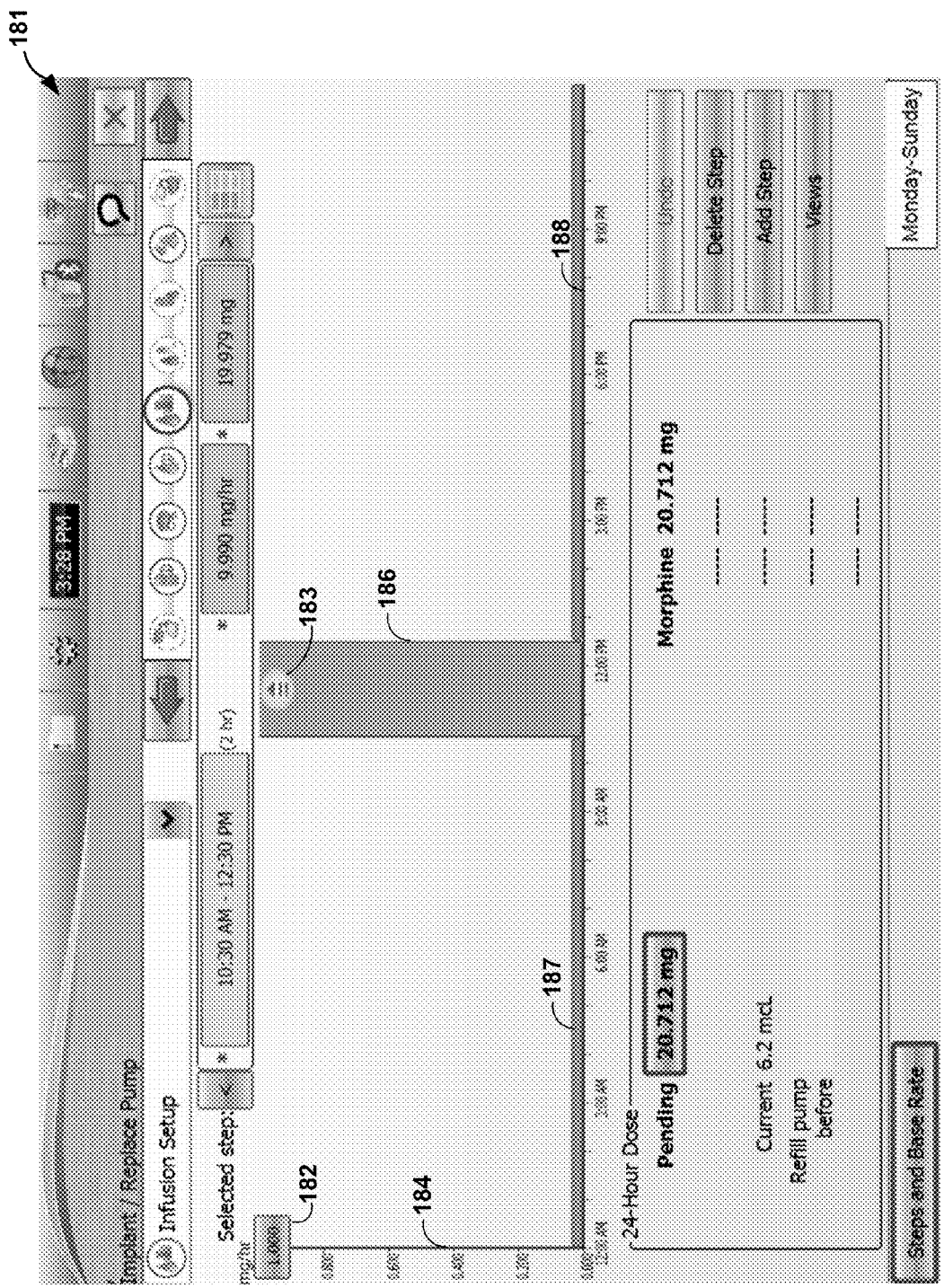
FIG. 11 is a screenshot illustrating an example graphical interface screen presented by an external programmer for displaying a current dosing program.
Figure 12:
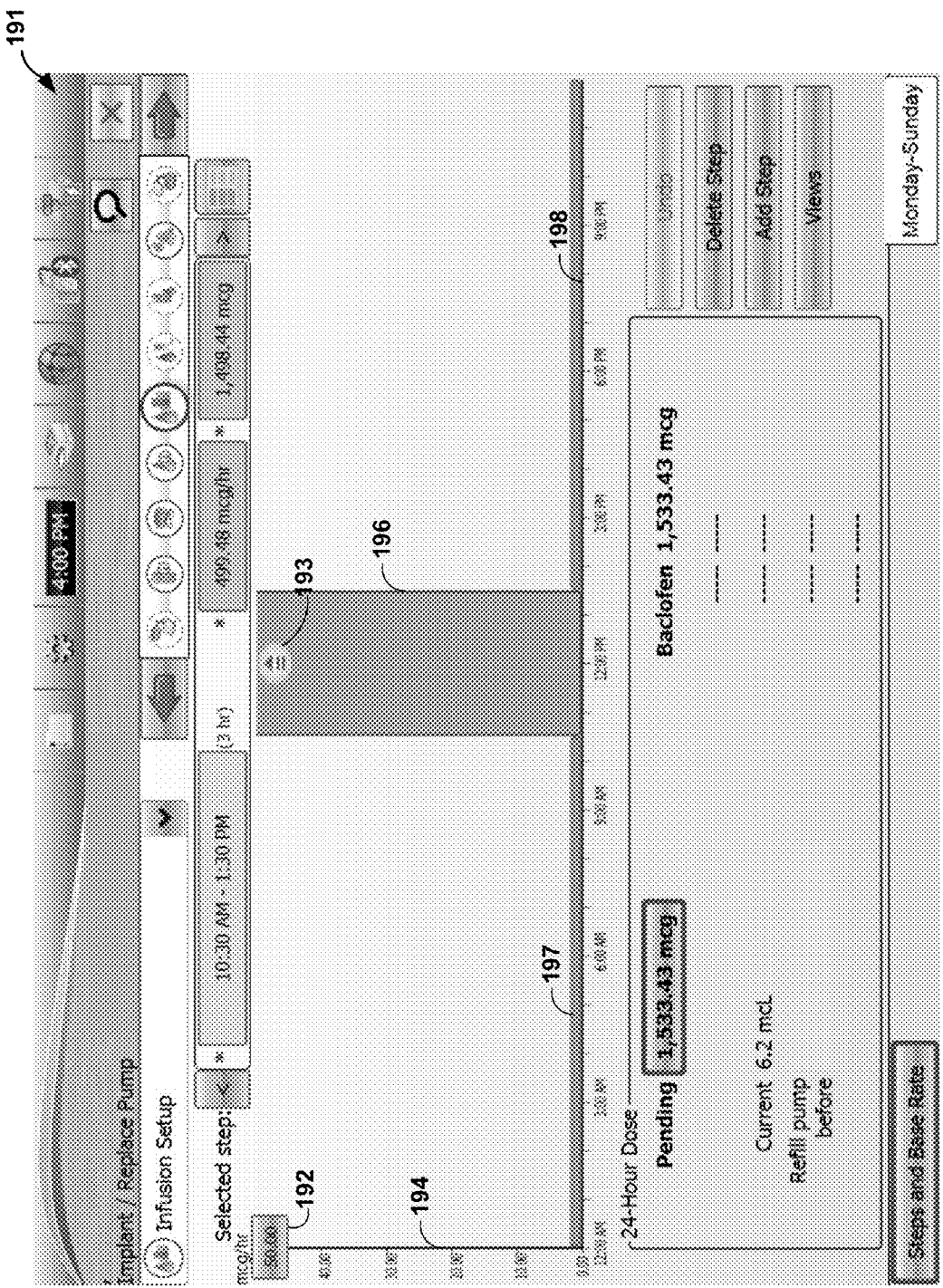
FIG. 12 is a screenshot illustrating an example graphical interface screen presented by an external programmer for displaying a current dosing program.

FIGS. 11 and 12 are screenshots illustrating example user interfaces which may be shown to a user by an implantable fluid delivery system. In some examples, the top portion of one or more of displayed graphical objects that correspond to a y-axis value may correspond to a y-axis value that is greater than the maximum displayed y-axis value. In such examples, the top portion of a graphical object may extend beyond the display range of the user interface screen. For example, FIGS. 11 and 12 depict two examples where the top portion of a graphical object extends beyond the display range of the user interface screen. FIG. 11 depicts y-axis 184, maximum y-axis value 182, graphical object 186, residual infusion rate element 187, and x-axis 188. FIG. 12 depicts y-axis 194, maximum y-axis value 192, graphical object 196, residual infusion rate element 197, and x-axis 198. In both FIGS. 11 and 12, the top portions of graphical objects 186 and 196 extend beyond the display range of user interface screens 181 and 191. Both FIGS. 11 and 12 depict a graphical icon, graphical icon 183 and 193 in FIGS. 11 and 12, respectively. In FIG. 11, graphical icon 183 provides visual notification to a user that the top portion of graphical object 186 extends beyond the display range of user interface screen 181. In FIG. 12, graphical icon 193 provides visual notification to a user that the top portion of graphical object 196 extends beyond the display range of user interface screen 191. In such circumstances, it may be beneficial for a user to adjust the display range of the user interface screen, e.g., by adjusting the maximum y-axis value, such that the y-axis value corresponding to the top portion of the graphical object is within the range of rate values of the displayed y-axis, e.g. between the minimum and maximum y-axis values. In the examples of FIGS. 11 and 12, it may be beneficial for user to adjust maximum y-axis values 182 and 192 to be larger than current maximum y-axis values 182 and 192 of one milligram per hour (1 mg/hr) and 50 micrograms per hour (50 mcg/hr) in FIGS. 11 and 12, respectively.

Figure 13A:
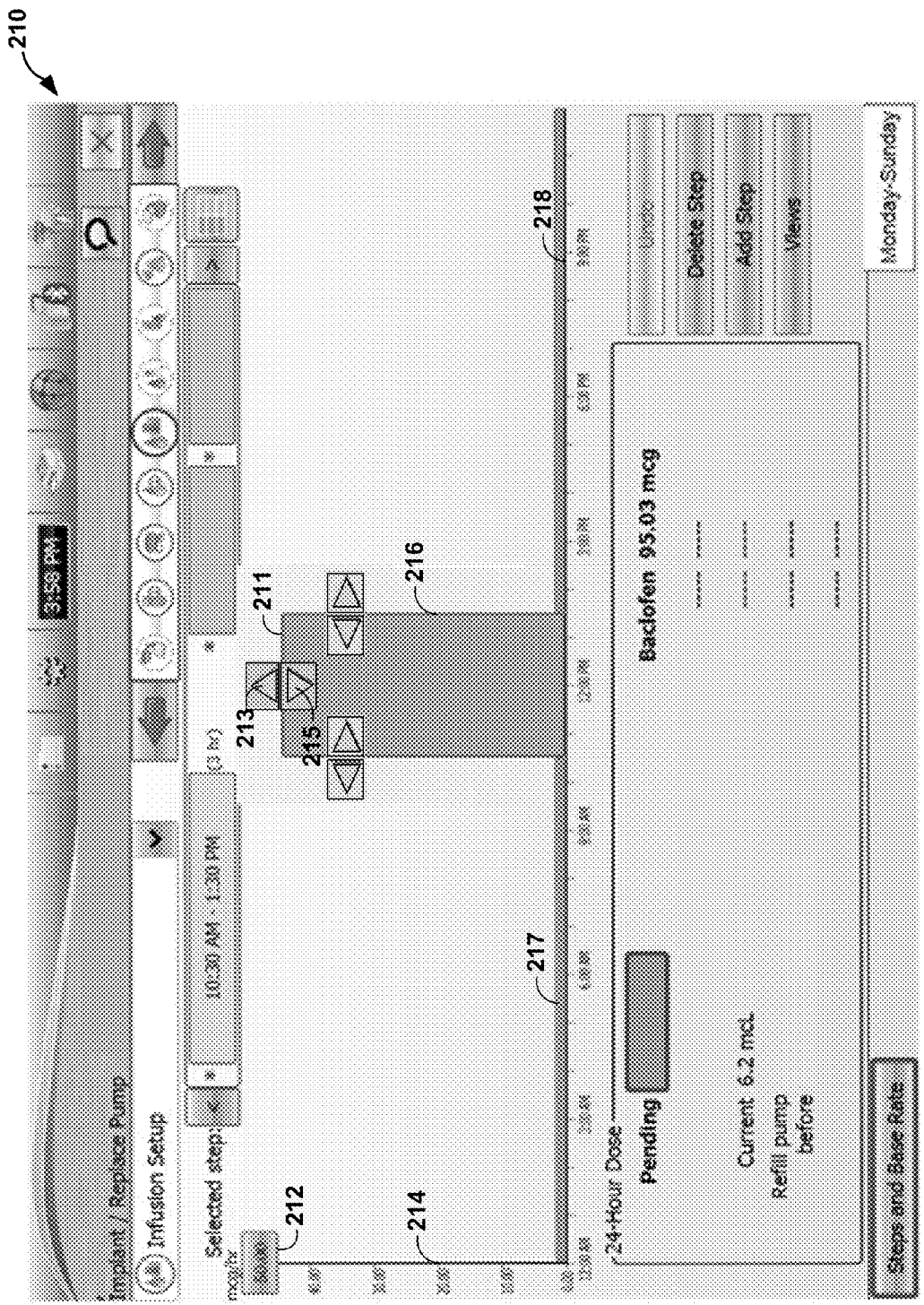
FIG. 13A is a screenshot illustrating an example graphical interface screen presented by an external programmer of a dosing program with a first displayed maximum vertical axis value.
Figure 13B:
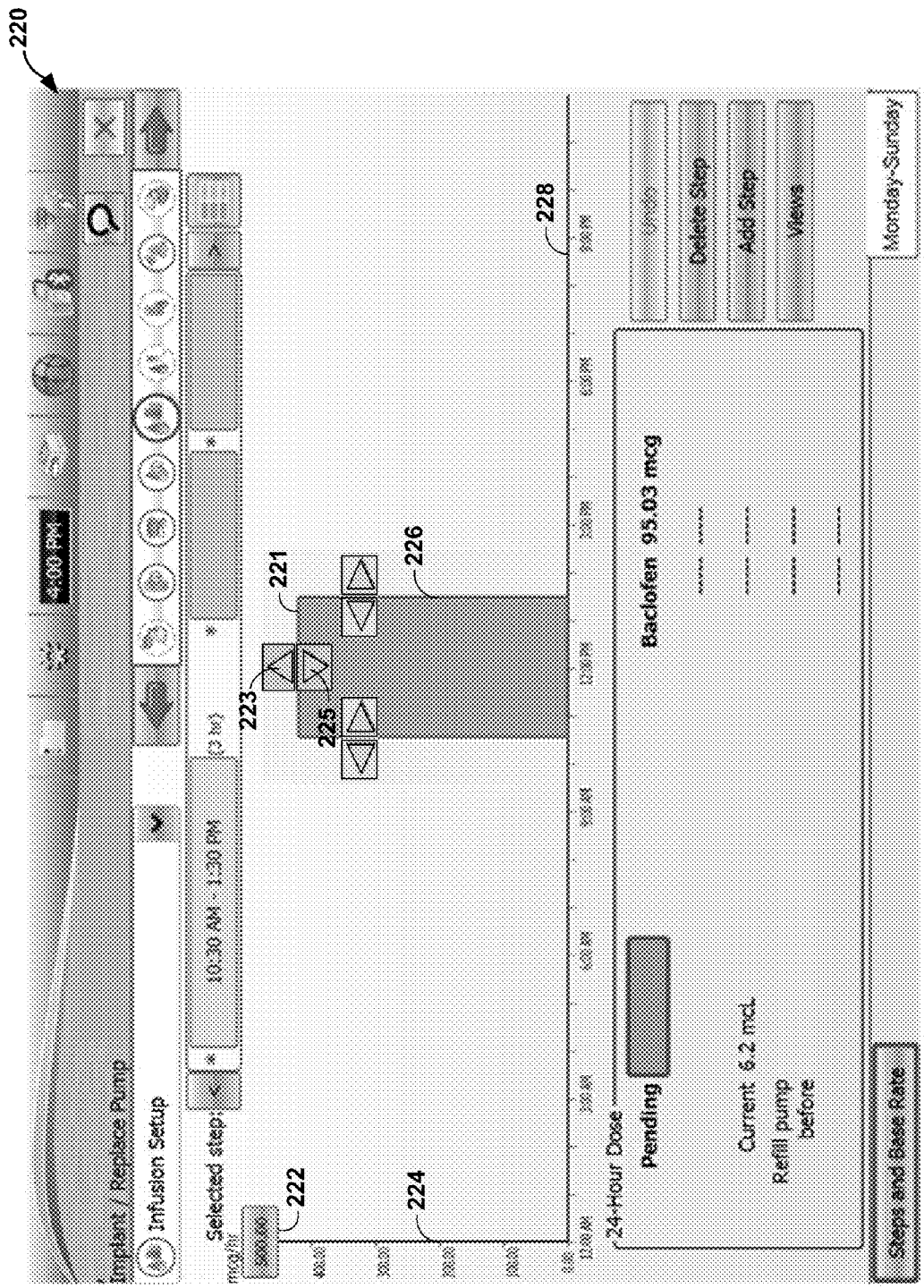
FIG. 13B is a screenshot illustrating an example graphical interface screen presented by an external programmer of a dosing program with a second displayed maximum vertical axis value.

FIGS. 13A and 13B are screenshots illustrating example user interfaces by which a user may modify an infusion pattern. In some examples, processor 52 may automatically determine a first reference rate value, in accordance with the techniques describe previously, and may cause a user interface to display a maximum y-axis value according to the determined reference rate value. In some examples, a user may adjust the top portion of a graphical object of a dosing program. In such examples, the top portion, corresponding to a first y-axis value, may be adjusted such that, after the adjustment, the top portion corresponds to a second y-axis value. Processor 52 may then determine a second reference rate value based on the second y-axis value. In some examples, processor 52 may determine the second reference rate value such that the second y-axis value corresponds to a fixed percent of the second reference rate value.

In the example of FIG. 13A, graphical object 216 represents the tallest graphical object in the dosing program displayed by user interface 210. User interface 210 depicts y-axis 214 representing rate values with a maximum y-axis value 212 of fifty milligrams per hour (50 mg/hr). User interface 210 also depicts x-axis 218 representing time, top portion 211 of graphical object 216, and first arrow 213 and second arrow 215, along with residual infusion rate 217. Top portion 211 of graphical object 216 corresponds to a first y-axis value of 45 milligrams per hour (45 mg/hr). In this example, forty-five milligrams per hour (45 mg/hr) represents ninety percent (90%) of the maximum y-axis value of fifty milligrams per hour (50 mg/hr). A user may select first arrow 213 of a dose adjustment button of graphical object 216. By selecting first arrow 213, the user may adjust top portion 211 of graphical object 216 to increase the height of top portion 211 of graphical object 216. After adjusting top portion 211 of graphical object 216, top portion 211 of graphical object 216 may correspond to a second y-axis value that is higher than the first y-axis value.

Processor 52 may determine a second reference rate value such that the second y-axis value corresponding to top portion 211 of graphical object 216 represents ninety percent (90%) of the determined second reference rate value. In other examples, processor 52 may determine one or more rate values such that top portion 211 of graphical object 216 corresponds to y-axis values that represent varying percents of the determined second reference rate value. For example, processor 52 may determine one or more rate values such that top portion 211 of graphical project 216 represent between approximately five (5%) and approximately ninety percent (90%) of the determined second reference rate value. In some examples, processor 52 may determine one or more rate values such that top portion 211 of graphical object 216 represent approximately five percent (5%), ten percent (10%), fifteen percent (15%), twenty percent (20%), twenty five percent (25%), fifty percent (50%), sixty percent (60%), seventy percent (70%), seventy five percent (75%), eighty percent (80%), or ninety percent (90%) of the determined second reference rate value.

FIG. 13B represents user interface 220 after top portion 211 of graphical object 216 has been adjusted to a higher level. In this example, user interface 220 depicts y-axis 224 representing rate values with a maximum y-axis value 222 of five hundred milligrams per hour (500 mg/hr). User interface 220 also depicts x-axis 228 representing time, graphical object 226 and top portion 221 of graphical object 226, and first arrow 223 and second arrow 225. In this example, the user has adjusted top portion 211 of graphical object 216 to correspond to a second y-axis value of four hundred and fifty milligrams per hour (450 mg/hr). Accordingly, processor 52 has determined at a second reference value such that the second y-axis rate value represents ninety percent (90%) of the determined second reference rate value. Processor 52 has then caused user interface device 50 to display user interface 220 with a new y-axis maximum value 222 of five hundred milligrams per hour (500 mg/hr). In this manner, processor 52 may be configured to adjust the maximum y-axis value automatically in response to a change in the height of the tallest graphical object of a dosing program such that the top portion of the tallest graphical object represents a fixed percent of the determined reference rate value. As described with respect to other techniques of the present disclosure, processor 52 may cause user interface devices 50 to display graphical user interfaces with a maximum y-axis value based on the reference rate values, and, in some instances, display graphical user interfaces with a maximum y-axis value that is a determined reference rate value. It should be understood that the FIGS. 13A and 13B only represent one example. In other examples, processor 52 may determine a new maximum y-axis rate such that the second y-axis value corresponding to top portion 221 of graphical object 226 represents other percent values of the second reference rate value.

In other examples, a user may adjust the maximum y-axis value, and accordingly, the displayed scale of an infusion graph, according to a free form zoom element. After selecting a displayed element, such as maximum y-axis value element 122 or 132 of FIGS. 5A-B and 6A-B, respectively, processor 52 may cause user interface 50 to display a free form zoom element. The free form zoom element may be a sliding scale element comprising a first end point, a second endpoint, and a first element initially positioned approximately halfway between the endpoints. A user may slide the first element within the free form zoom element in a first direction toward the first endpoint or in a second direction toward to the second endpoint. In some example, as a user slides the first element in the first direction, processor 52 may cause user interface 50 to display the infusion graph with a new maximum y-axis value greater than the current maximum y-axis value, and therefore, at larger scale. Also in some examples, as a user slides the first element in the second direction, processor 52 may cause user interface 50 to display the infusion graph with decreasing maximum y-axis values, and therefore, a smaller scale. For example, as a user slides the first element in the first direction, processor 52 may receive an indication that a user has slid the first element a certain distance toward the first endpoint and increase the maximum y-axis value, and, accordingly, the scale of the infusion graph. Processor 52 may cause a similar adjustment after receiving an indication that a user has slid the first element a certain distance toward the second endpoint, except processor 52 may cause user interface 50 to display a smaller maximum y-axis value and, accordingly, a smaller scale of the infusion graph. As the user continues to slide the first element further from the initial position of the first element toward one of the endpoints, processor 52 may cause user interface 50 to display additional infusion graphs with even greater or smaller maximum y-axis values. In this manner, a user may adjust the maximum and minimum y-axis values according to a free form zoom element by sliding a first element in a first or a second direction.

In other examples, after receiving a selection of a displayed element, such as maximum y-axis value element 122 or 132 of FIGS. 5A-B and 6A-B, respectively, processor 52 may cause user interface 50 to display a tall zoom element and a short zoom element. In some examples, upon receiving a selection of the tall zoom element, processor 52 may cause user interface 50 to display the y-axis of the infusion graph with a new maximum y-axis value such that none of the top portions of the tallest graphical objects in the infusion graph corresponding to y-axis values above the new maximum y-axis value. Additionally, processor 52 may cause user interface 50 to display the y-axis with a new minimum y-axis value greater than zero. Accordingly, after displaying the infusion graph with the new maximum and minimum y-axis values, the graphical objects with top portions corresponding to y-axis values smaller than the new minimum y-axis value may not be displayed in the infusion graph. Alternatively, upon receiving a selection of the short zoom element, processor 52 may cause user interface 50 to display the y-axis of the infusion graph with a new maximum y-axis value where the new maximum y-axis value is less than the y-axis value corresponding to at least one top portion of a graphical object in the infusion graph. Accordingly, after displaying the infusion graph with the new maximum and minimum y-axis values, the graphical objects with top portions corresponding to y-axis values greater than the new minimum y-axis value may not be displayed in the infusion graph. In some examples, processor 52 may determine an average rate value comprising the average of all of the y-axis values corresponding to the top portions of the graphical objects in an infusion graph. Processor 52 may then cause user interface 50 to display the y-axis of the infusion graph with a new maximum y-axis value corresponding to the determined average rate value. Accordingly, user interface 50 may not display the top portions of any graphical objects with top portions corresponding to y-axis values greater than the new maximum y-axis value. Rather, in some examples, user interface 50 may display a graphical icon, such as graphical icon 183 or 193 of FIGS. 11 and 12, respectively, indicating that a portion of the graphical object corresponds to y-axis values greater than the current maximum y-axis value. In other examples, processor 52 may cause user interface 50 to display the y-axis of the infusion graph with a new minimum y-axis value corresponding to the determined average rate, which would result in any graphical objects with top portions corresponding to y-axis value smaller than the determined average rate to not be displayed in the infusion graph.

Also in some examples, user interface 50 may display a dosing program comprising two separate infusion graphs. For example, user interface 50 may display a first infusion graph comprising a first x-axis corresponding to time and a first y-axis corresponding to infusion rate values. User interface 50 may further display a second infusion graph comprising a second x-axis corresponding to time and a second y-axis corresponding to infusion rate values. In some examples, the two graphs may represent a single dosing program. That is, the two infusion graphs may represent the same dosing program, but the displayed graphs may have differing scales. For example, both infusion graph x-axes may span the same time period, such as from 12:00 am to 11:59 pm. The y-axis of the first infusion graph may have a first minimum y-axis value of zero and a first y-axis maximum value. The y-axis of the second infusion graph may have a second minimum y-axis value greater than the first y-axis maximum value and a second y-axis maximum value (which is greater than the second y-axis minimum value). Accordingly, each of the infusion graphs may display a different portion of the same dosing program. The first infusion graph may display information about the dosing program corresponding to relatively lower y-axis values while the second infusion graph may display information about the dosing program corresponding to relatively higher y-axis values. Additionally, in each of the above described examples, processor 52 may cause user interface 50 to display any of the elements or icons described with respect to FIGS. 5A-13B. Each of the above described examples may further include any of the operational functions described with respect to FIGS. 5A-13B.

Figure 14:
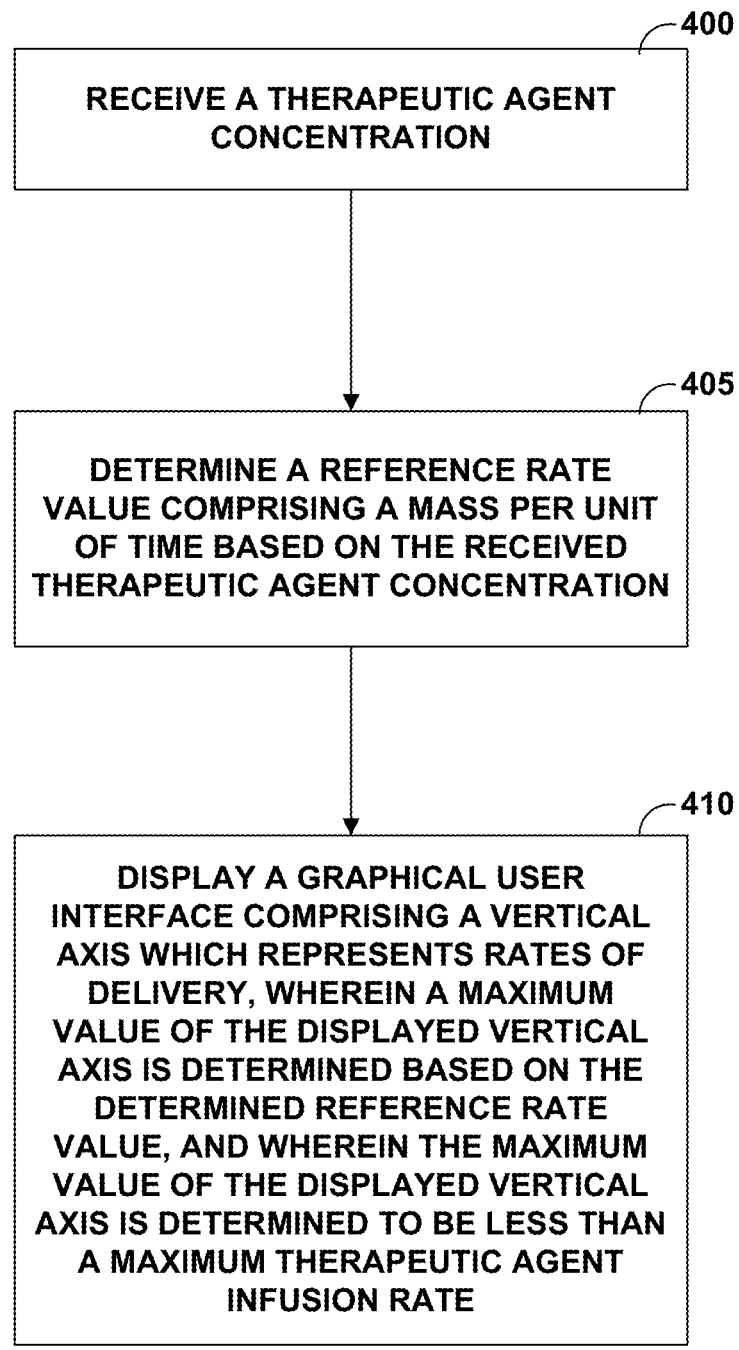
FIG. 14 is a flowchart illustrating an example method for determining rate values based on a selected therapeutic agent concentration value.

FIG. 14 is a flowchart illustrating an example method for determining one or more rate values based on therapeutic concentration input. Although discussed with respect to programmer 20 and IMD 12, it should be understood that any implantable medical device, and any device for programming the IMD, may implement the example method of FIG. 14.

Initially, programmer 20 receives a therapeutic agent concentration (400). For example a user may load a therapeutic agent into IMD 12. Additionally, the user may input into programmer 20 the specific therapeutic agent and the concentration at which the therapeutic agent is stored within IMD 12. Programmer 20 also determines a reference rate value comprising a mass per unit of time based on the received therapeutic concentration (405). In some examples, programmer 20 determines mass values of the reference rate value to be varying percents of the mass value of the received therapeutic concentration and programmer 20 may determine the unit of time to be one hour. Some example percents may range from approximately two-tenths (0.2%) of a percent to approximately twenty percent (20%). For example, the therapeutic agent concentration may be expressed in mass units per volume units. One example therapeutic concentration may be ten milligrams per milliliter (10 mg/mL). Accordingly, programmer 20 determines a reference rate value to include a mass value that is ten percent of the mass value of the therapeutic agent concentration. In the example where the therapeutic agent concentration is ten milligrams per milliliter (10 mg/mL), programmer 20 determines a reference rate value to be one milligram per hour (1 mg/hr). In this example, the one milligram mass unit of the reference rate value is ten percent of the ten milligram mass value of the therapeutic agent concentration. It should be understood that programmer 20 may determine different multiple reference rate values according to varying percents, in accordance with the techniques described herein.

Programmer 20 further displays a graphical user interface comprising a vertical axis which represents rates of delivery, wherein a maximum value of the displayed vertical axis is determined based on the determined reference rate value, and wherein the maximum value of the displayed vertical axis is determined to be less than a maximum therapeutic agent infusion rate (410). In some examples, programmer 20 may automatically display the graphical interface based on the determined reference rate value, e.g., causing user interface device 50 to display a graphical user interface including a vertical axis, wherein the maximum vertical axis value is determined based on the determined reference rate value. In some examples, the maximum vertical axis value is the determined reference rate value. In this manner, programmer 20 automatically determines a scale for the vertical axis of the graphical display based on the received therapeutic agent concentration and displays the graphical user interface with a vertical axis according to the scale.

Figure 15:
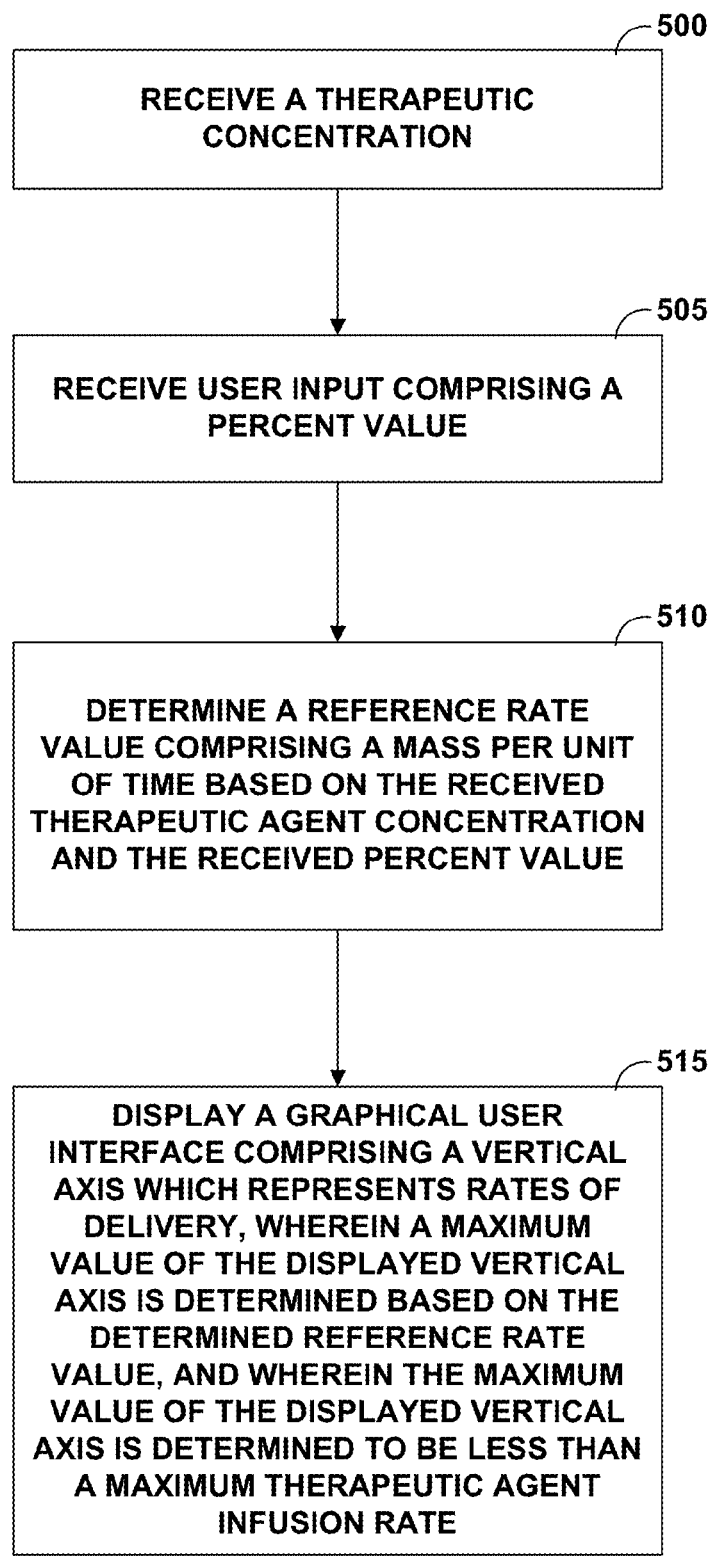
FIG. 15 is a flowchart illustrating an example method for determining rate values based on a selected therapeutic agent concentration value.

FIG. 15 is a flowchart illustrating an example method for determining one or more rate values based on a received therapeutic concentration and a received input percent. Although discussed with respect to programmer 20 and IMD 12, it should be understood that any implantable medical device, and any device for programming the IMD, may implement the example method of FIG. 15.

As described with respect to FIG. 14, initially, programmer 20 receives a therapeutic agent concentration (500). In the example method of FIG. 15, programmer 20 further receives user input comprising a percent value (505). The percent value may specify a particular percent for use in determining the reference rate value. As described previously, in the examples of FIG. 14 and other figures, programmer 20 determines the reference rate value to include a mass value of varying percents of the mass value of the received therapeutic agent concentration. However, instead of automatically determining a reference rate value based on predetermined percents of the therapeutic agent concentration, processor 52 may additionally receive user input comprising a specific percent value and determine the reference rate value based on the received therapeutic agent concentration and the received percent value.

Accordingly, programmer 20 determines a reference rate value comprising a mass per unit of time based on the received therapeutic concentration and the received percent value (510). For example, the therapeutic agent concentration may be five hundred micrograms per milliliter (500 mcg/mL). Additionally, a user may input a percent value of twenty-five percent (25%). Programmer 20 then determines a reference rate value including a mass value that is twenty percent (25%) of the mass value of the therapeutic agent concentration. In this example, programmer 20 determines that the reference rate value is one hundred and twenty five micrograms per hour (125 mcg/hr), using the assumption that programmer 20 determines the period of time for the reference rate value to be one hour.

Programmer 20 further displays a graphical user interface comprising a horizontal axis and a vertical axis, wherein the vertical axis which represents rates of delivery, wherein a maximum value of the displayed vertical axis is determined based on the determined reference rate value, and wherein the maximum value of the displayed vertical axis is determined to be less than a maximum therapeutic agent infusion rate (515). In some examples, programmer 20 may automatically display the graphical interface based on the determined reference rate value, e.g., causing user interface device 50 to display a graphical user interface including a vertical axis, wherein the maximum vertical axis value is determined based on the determined reference rate value. In some examples, the maximum vertical axis value is the determined reference rate value. In this manner, programmer 20 automatically determines a scale for the vertical axis of the graphical display based on the received therapeutic agent concentration and the received percent value and displays the graphical user interface with a vertical axis according to the scale.

Figure 16:
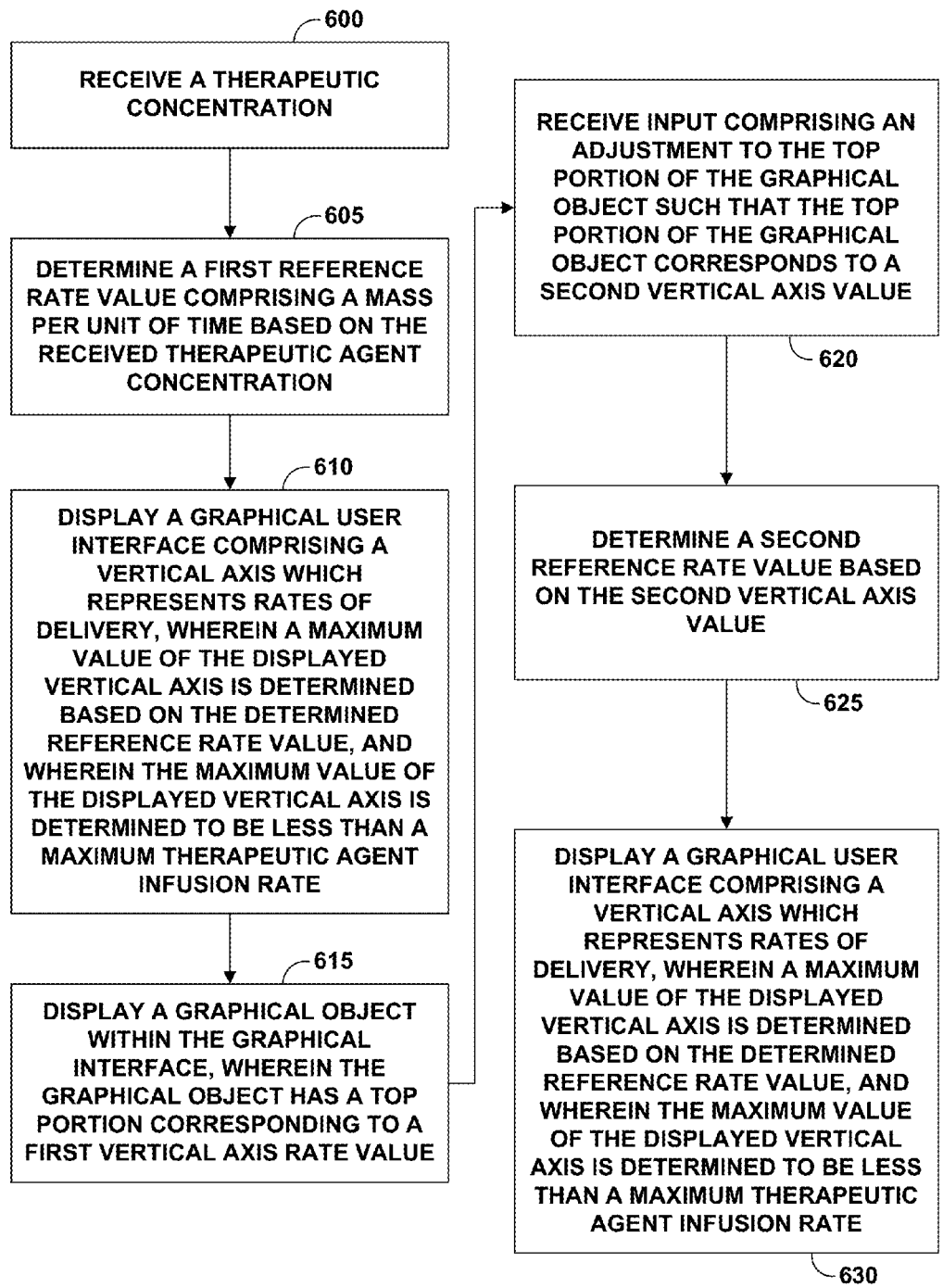
FIG. 16 is a flowchart illustrating an example method for determining one or more rate values based on an adjustment to a dosing program dosing parameter

FIG. 16 is a flowchart illustrating an example method for determining one or more rate values based on an adjustment to a dosing program dosing parameter. Although discussed with respect to programmer 20 and IMD 12, it should be understood that any implantable medical device, and any device for programming the IMD, may implement the example method of FIG. 16.

As described with respect to FIG. 14, programmer 20 receives a therapeutic agent concentration (600), determines a first reference rate value comprising a mass per unit of time based on the received therapeutic concentration input (605), and displays a graphical interface comprising a vertical axis which represents rates of delivery, wherein a maximum value of the displayed vertical axis is determined based on the determined first reference rate value, and wherein the maximum value of the displayed vertical axis is determined to be less than a maximum therapeutic agent infusion rate (610).

In the method of FIG. 16, programmer 20 further displays a graphical object including a top portion within the graphical interface, wherein the top portion corresponds to a vertical axis value (615). In some examples, the graphical interface displayed by programmer 20 is a bar chart and the graphical object is a bar. In these examples, the top of the bar correspond to a vertical axis value. Additionally, in some examples, the graphical object may comprise one or more buttons that allow a user to adjust features of the bar such as the width and height of the bar. Accordingly, at a first position, the top portion of the graphical object may correspond to a first vertical axis value. Programmer 20, e.g., via user interface 50, may receive input comprising an adjustment to the top portion of the graphical figure such that the top portion of the graphical object corresponds to a second vertical axis value (620). For example, a user may adjust the top portion of a bar to correspond to a second vertical axis value, either higher than or lower than the first vertical axis value.

Programmer 20 further determines a second reference rate value based on the second vertical axis value (625). In some examples, programmer 20 may determine a second reference rate value such that the second vertical axis value corresponds to a fixed percentage of the determined second reference rate value. For example, programmer 20 may determine the second reference rate value such that the second vertical axis rate value corresponds to ninety percent of the determined second reference rate value. Instead, programmer 20 may determine one or more other or additional reference rate values such that the second vertical axis rate value corresponds to different fixed percents of the one or more other or additional reference rate values. As an illustrative example, the therapeutic agent concentration may be ten milligrams per hour (10 mg/hr). Accordingly, programmer 20 determines a second reference rate value such that the second vertical axis rate value corresponds to fifty percent of the determined second reference rate value. In this example, programmer 20 determines the second reference rate value to be twenty milligrams per hour (20 mg/hr). In other examples, programmer 20 may determine other reference rate values such that the second vertical axis rate value corresponds to different percents of the determined second reference rate value.

Programmer 20 further displays the graphical interface comprising a vertical axis, wherein the maximum value of the displayed vertical axis that is determined based on the determined second reference rate value, and wherein the maximum value of the displayed vertical axis is determined to be less than a maximum therapeutic agent infusion rate (630). In this manner, programmer 20 automatically scales the graphical interface according to the adjusted graphical object. This helps to ensure that a user may easily read the graphical display and determine the dosing parameters. Automatically adjusting the graphical interface also assists users in being able to more easily select the various buttons present in the graphical interface, such as the dosing adjustment buttons, because the sizing of the graphical figure relative to the graphical interface may ensure sufficient spacing between the various buttons for easy selection.

The techniques described herein, although described with respect to a fluid delivery system, may be used in other therapy devices. For example, the techniques described herein may be useful in any therapy system that benefits from implementing a graphical programming method where a device of the system displays a therapy parameter varying on a vertical scale. For example, some electrical stimulation devices may benefit by allowing a user to adjust therapy parameters (e.g., voltage or current) using a graphical interface instead of entering text data.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of this disclosure have been described. These and other embodiments are within the scope of the following claims.

What is claimed:
1. A method comprising:
   receiving, by a device for programming a fluid delivery device, a therapeutic agent concentration, wherein the therapeutic agent concentration indicates a mass of a therapeutic agent per unit of volume of a fluid delivered by the fluid delivery device;
   determining, by the device for programming the fluid delivery device, a maximum rate value of a vertical axis for display via a user interface of the device based on the received therapeutic agent concentration, wherein the vertical axis represents rates of delivery of the fluid by the fluid delivery device, wherein the maximum rate value includes a mass value, wherein determining the maximum rate value of the vertical axis based on the received therapeutic agent concentration comprises determining the mass value of the maximum rate value as a percent of the mass value indicated by the therapeutic agent concentration;
   displaying, via the user interface, a horizontal axis and the vertical axis, wherein the horizontal axis represents time, and wherein the maximum rate value of the displayed vertical axis is determined to be less than a maximum therapeutic agent infusion rate; and
   displaying an indication of a therapy dosing program for delivery of the therapeutic agent to a patient relative to the horizontal axis and the vertical axis to represent a rate of delivery of the therapeutic agent via the fluid delivery device to the patient over time.

2. The method of claim 1, wherein determining the maximum rate value based on the received therapeutic agent concentration comprises:
   determining a plurality of maximum rate values, wherein respective mass values for the plurality of maximum rate values are determined as a respective percent of the mass value indicated by the therapeutic agent concentration, and
   selecting one of the maximum rate values as the determined maximum rate value for display.

3. The method of claim 2, wherein selecting the one of the maximum rate values as the determined maximum rate value comprises automatically selecting the one of the maximum rate values as the determined maximum rate value.

4. The method of claim 2, wherein selecting the one of the maximum rate values as the determined maximum rate value comprises selecting the one of the maximum rate values as the determined maximum rate value based on user input.

5. The method of claim 1, wherein determining the mass value of the maximum rate value as a percent of the mass value indicated by the therapeutic agent concentration comprises determining the mass value between approximately 0.2% and approximately 20% of the mass value of the received therapeutic agent concentration.

6. The method of claim 1, wherein determining the mass value of the maximum rate value as a percent of the mass value indicated by the therapeutic agent concentration comprises determining the reference rate value to comprise a mass value of approximately 0.2%, 2.5%, 5% 10%, 15%, or 20% of the mass value of the received therapeutic agent concentration.

7. The method of claim 1, further comprising:
displaying, with the device for programming the fluid delivery device and in the graphical interface, a zoom element;
upon receiving a selection of the zoom element, displaying, by the device for programming the fluid delivery device and in the graphical interface, one or more maximum vertical axis values, wherein the one or more maximum vertical axis values comprise at least the determined maximum rate value; and
upon receiving a selection of one of the displayed one or more maximum vertical axis values, displaying, with the device for programming the fluid delivery device, in the graphical user interface, the maximum rate value of the vertical axis as the selected maximum vertical axis value.

8. The method of claim 1, wherein the maximum rate value comprises a first maximum rate value, wherein displaying an indication of a therapy dosing program for delivery of the therapeutic agent to a patient relative to the horizontal axis and the vertical axis comprises displaying, by the device for programming the fluid delivery device and in the graphical interface, a graphical figure including a top portion that corresponds to a first vertical axis rate value, the method further comprising:
receiving, by the device for programming the fluid delivery device, an input comprising an adjustment to the top portion of the graphical figure, wherein, after adjusting the top portion of the graphical figure, the top portion of the graphical figure corresponds to a second vertical axis rate value;
determining a second maximum rate value for the vertical axis based on the second vertical axis value; and
displaying, by the device for programming the fluid delivery device, the horizontal axis and the vertical axis according to the second maximum rate value.

9. The method of claim 1,
wherein displaying an indication of a therapy dosing program for delivery of the therapeutic agent to a patient relative to the horizontal axis and the vertical axis comprises displaying, by the device for programming the fluid delivery device and in the graphical interface, a graphical figure including a top portion that corresponds to a vertical axis rate value,
the method further comprising displaying, by the device for programming the fluid delivery device and in the graphical interface, a graphical icon when the top portion of the graphical figure corresponds to a vertical axis rate value greater than the maximum vertical axis rate value.

10. The method of claim 1, wherein the fluid delivery device includes an implantable fluid delivery device.

11. The method of claim 1, further comprising determining the proposed therapy dosing program based on the received therapeutic agent concentration.

12. A programmer device comprising:
a user interface comprising a display to present a graphical representation of delivery of a therapeutic agent to a patient via a fluid by a fluid delivery device, wherein the user interface displays a horizontal axis and a vertical axis, wherein the horizontal axis represents time and the vertical axis represents rates of delivery of the fluid by the fluid delivery device; and
a processor configured to:
receive a therapeutic agent concentration, wherein the therapeutic agent concentration indicates a mass of a therapeutic agent per unit of volume of a fluid delivered by the fluid delivery device,
determine a maximum rate value of the vertical axis for display in the user interface based on the received therapeutic agent concentration, wherein the maximum rate value includes a mass value, wherein the processor is configured to determine the mass value of the maximum rate value as a percent of the mass value indicated by the therapeutic agent concentration,
control the user interface to display the horizontal axis and the vertical axis including the maximum rate value of the vertical axis, wherein the maximum rate value of the displayed vertical axis is determined to be less than a maximum therapeutic agent infusion rate, and
control the user interface to display an indication of a therapy dosing program for delivery of the therapeutic agent to a patient relative to the horizontal axis and the vertical axis to represent a rate of delivery of the therapeutic agent via the fluid delivery device to the patient over time.

13. The programmer of claim 12, wherein the processor is configured to determine a plurality of maximum rate values, wherein respective mass values for the plurality of maximum rate values are determined as a respective percent of the mass value indicated by the therapeutic agent concentration, and to select one of the maximum rate values as the determined maximum rate value for display.

14. The programmer of claim 13, wherein the processor is configured to select the one of the maximum rate values as the determined maximum rate value automatically.

15. The programmer of claim 13, wherein the processor is configured to select the one of the maximum rate values as the determined maximum rate value based on user input.

16. The programmer of claim 12, wherein the processor is configured to determine the mass value between approximately 0.2% and approximately 20% of the mass value of the received therapeutic agent concentration.

17. The programmer of claim 12, wherein the processor is configured to determine the mass value of approximately 0.2%, 2.5%, 5%, 10%, 15%, and 20% of the mass value of the received therapeutic agent concentration.

18. The programmer of claim 12, wherein the processor is configured to:
control the user interface to display a zoom element;
upon receiving a selection of the zoom element, control the user interface to display one or more maximum vertical axis values, wherein the one or more maximum vertical axis values comprise at least the determined maximum rate value; and
upon receiving a selection of one of the one or more maximum vertical axis values, control the user interface to display in the graphical user interface, the maximum rate value of the vertical axis as the selected maximum vertical axis value.

19. The programmer of claim 12, wherein the reference rate value comprises a first reference rate value, and wherein the processor is configured to:
control the user interface to display a graphical figure including a top portion that corresponds to a first vertical axis rate value;
receive input comprising an adjustment to the top portion of the graphical figure, wherein, after adjusting the top portion of the graphical figure, the top portion of the graphical figure corresponds to a second vertical axis rate value;

determine a second maximum rate value for the vertical axis based on the second vertical axis value; and control the user interface to display the graphical user interface comprising the horizontal axis and the vertical axis according to the second maximum rate value.

20. The programmer of claim 12, wherein the processor is configured to:
control the user interface to display a graphical figure including a top portion that corresponds to a vertical axis rate value; and
control the user interface to display a graphical icon when the top portion of the graphical figure corresponds to a vertical axis rate value greater than the maximum vertical axis value.

21. The programmer device of claim 12, wherein the fluid delivery device includes an implantable fluid delivery device.

22. A system comprising:
a fluid delivery device; and
a programmer device configured to program the fluid delivery device, the programmer device comprising:
a user interface comprising a display to present a graphical representation of delivery of a therapeutic agent to a patient via a fluid by an implantable fluid delivery device, wherein the user interface displays a horizontal axis and a vertical axis, wherein the horizontal axis represents time and the vertical axis represents rates of delivery of the fluid by the implantable fluid delivery device; and
a processor configured to:
receive a therapeutic agent concentration, wherein the therapeutic agent concentration indicates a mass of a therapeutic agent per unit of volume of a fluid delivered by the fluid delivery device,
determine a maximum rate value of the vertical axis for display in the user interface based on the received therapeutic agent concentration, wherein the maximum rate value includes a mass value, wherein the processor is configured to determine the mass value of the maximum rate value as a percent of the mass value indicated by the therapeutic agent concentration,
control the user interface to display the horizontal axis and the vertical axis including the maximum rate value of the vertical axis, wherein the maximum rate value of the displayed vertical axis is determined to be less than a maximum therapeutic agent infusion rate, and
control the user interface to display an indication of the therapy dosing program for delivery of the therapeutic agent to a patient relative to the horizontal axis and the vertical axis to represent a rate of delivery of the therapeutic agent via the fluid delivery device to the patient over time.

23. The system of claim 22, wherein the processor is configured to determine a plurality of maximum rate values, wherein respective mass values for the plurality of maximum rate values are determined as a respective percent of the mass value indicated by the therapeutic agent concentration, and to select one of the maximum rate values as the determined maximum rate value for display.

24. The system of claim 23, wherein the processor is configured to select the one of the maximum rate values as the determined maximum rate value automatically.

25. The system of claim 23, wherein the processor is configured to select the one of the maximum rate values as the determined maximum rate value based on user input.

26. The system of claim 22, wherein the processor is configured to determine the mass value between approximately 0.2% and approximately 20% of the mass value of the received therapeutic agent concentration.

27. The system of claim 22, wherein the processor is configured to determine the mass value of approximately 0.2%, 2.5%, 5%, 10%, 15%, and 20% of the mass value of the received therapeutic agent concentration.

28. The system of claim 22, wherein the processor is configured to:
control the user interface to display a zoom element;
upon receiving a selection of the zoom element, control the user interface to display one or more maximum vertical axis values, wherein the one or more maximum vertical axis values comprise at least the determined maximum rate value; and
upon receiving a selection of one of the one or more maximum vertical axis values, control the user interface to display in the graphical user interface, the maximum rate value of the vertical axis as the selected maximum vertical axis value.

29. The system of claim 22, wherein the reference rate value comprises a first reference rate value and wherein the processor is configured to:
control the user interface to display a graphical figure including a top portion that corresponds to a first vertical axis rate value;
receive input comprising an adjustment to the top portion of the graphical figure, wherein, after adjusting the top portion of the graphical figure, the top portion of the graphical figure corresponds to a second vertical axis rate value;
determine a second maximum rate value for the vertical axis based on the second vertical axis value; and
control the user interface to display the graphical user interface comprising the horizontal axis and the vertical axis according to the second maximum rate value.

30. The system of claim 22, wherein the processor is configured to:
control the user interface to display a graphical figure including a top portion that corresponds to a vertical axis rate value; and
control the user interface to display a graphical icon when the top portion of the graphical figure corresponds to a vertical axis rate value greater than the maximum vertical axis value.

31. The system of claim 22, wherein the fluid delivery device includes an implantable fluid delivery device.

32. A medical device comprising:
means for receiving a therapeutic agent concentration, wherein the therapeutic agent concentration indicates a mass of the therapeutic agent per unit of volume of a fluid delivered by a fluid delivery device;
means for determining a maximum rate value of a vertical axis for display via a user interface of the device based on the received therapeutic agent concentration, wherein the vertical axis represents rates of delivery of the fluid by the fluid delivery device, wherein the maximum rate value includes a mass value, wherein the means for determining the maximum rate value of the vertical axis based on the received therapeutic agent concentration comprises means for determining the mass value of the maximum rate value as a percent of the mass value indicated by the therapeutic agent concentration;
means for displaying a horizontal and the vertical axis, wherein the horizontal axis represents time, and wherein the maximum rate value of the displayed vertical axis is determined to be less than a maximum therapeutic agent infusion rate; and means for displaying an indication of a therapy dosing program for delivery of the therapeutic agent to a patient relative to the horizontal axis and the vertical axis to represent a rate of delivery of the therapeutic agent via the fluid delivery device to the patient over time.

33. The medical device of claim 32, wherein the means for determining the mass value of the maximum rate value as a percent of the mass value indicated by the therapeutic agent concentration comprises means for determining the mass value between approximately 0.2% and approximately 20% of the mass value of the received therapeutic agent concentration.

34. The medical device of claim 32, wherein the means for determining the mass value of the maximum rate value as a percent of the mass value indicated by the therapeutic agent concentration comprises means for determining the mass value of approximately 0.2%, 2.5%, 5% 10%, 15%, or 20% of the mass value of the received therapeutic agent concentration.

35. The medical device of claim 32, wherein the maximum rate value comprises a first maximum rate value, the medical device further comprising:
a means for displaying a graphical figure including a top portion that corresponds to a first vertical axis rate value;
a means for receiving input comprising an adjustment to the top portion of the graphical figure, wherein, after adjusting the top portion of the graphical figure, the top portion of the graphical figure corresponds to a second vertical axis rate value;
a means for determining a second maximum rate value for the vertical axis based on the second vertical axis value; and
a means for displaying the graphical user interface comprising the horizontal axis and a vertical axis the vertical axis according to the second maximum rate value.

36. The medical device of claim 32, wherein the fluid delivery device includes an implantable fluid delivery device.

37. A non-transitory computer-readable storage medium comprising instructions for causing a programmable processor to:
receive, by a device for programming a fluid delivery device, a therapeutic agent concentration, wherein the therapeutic agent concentration indicates a mass of a therapeutic agent per unit of volume of a fluid delivered by the fluid delivery device;
determine a maximum rate value of the vertical axis for display in the user interface based on the received therapeutic agent concentration, wherein the maximum rate value includes a mass value, wherein the processor is configured to determine the mass value of the maximum rate value as a percent of the mass value indicated by the therapeutic agent concentration,
control the user interface to display the horizontal axis and the vertical axis including the maximum rate value of the vertical axis, wherein the maximum rate value of the displayed vertical axis is determined to be less than a maximum therapeutic agent infusion rate, and
control the user interface to display an indication of a therapy dosing program for delivery of the therapeutic agent to a patient relative to the horizontal axis and the vertical axis to represent a rate of delivery of the therapeutic agent via the fluid delivery device to the patient over time.

38. The non-transitory computer-readable medium of claim 37, wherein the instructions cause the processor to determine the mass value between approximately 0.2% and approximately 20% of the mass value of the received therapeutic agent concentration.

39. The non-transitory computer-readable medium of claim 37, wherein the instructions cause the processor to determine the mass value of approximately 0.2%, 2.5%, 5%, 10%, 15%, and 20% of the mass value of the received therapeutic agent concentration.

40. The non-transitory computer-readable medium of claim 37, wherein the fluid delivery device includes an implantable fluid delivery device.

* * * * *